United States Patent
Fu

(10) Patent No.: US 9,623,116 B2
(45) Date of Patent: Apr. 18, 2017

(54) ANTIBODY-LIGHT FUSION PRODUCTS FOR CANCER THERAPEUTICS

(71) Applicant: THE UNIVERSITY OF CHICAGO, Chicago, IL (US)

(72) Inventor: Yang-Xin Fu, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/717,808

(22) Filed: May 20, 2015

(65) Prior Publication Data

US 2015/0283260 A1    Oct. 8, 2015

Related U.S. Application Data

(62) Division of application No. 13/563,372, filed on Jul. 31, 2012, now Pat. No. 9,061,073, which is a division of application No. 12/599,946, filed as application No. PCT/US2008/006381 on May 14, 2008, now Pat. No. 8,263,081.

(60) Provisional application No. 60/917,852, filed on May 14, 2007.

(51) Int. Cl.
| | |
|---|---|
| *A61K 39/00* | (2006.01) |
| *A61K 39/395* | (2006.01) |
| *A61K 47/48* | (2006.01) |
| *C07K 14/525* | (2006.01) |
| *A61K 31/7088* | (2006.01) |
| *A61K 38/19* | (2006.01) |

(52) U.S. Cl.
CPC .... *A61K 47/48423* (2013.01); *A61K 31/7088* (2013.01); *A61K 38/191* (2013.01); *A61K 39/39558* (2013.01); *A61K 47/48569* (2013.01); *C07K 14/5255* (2013.01); *A61K 2039/505* (2013.01); *A61K 2039/507* (2013.01); *C07K 2319/33* (2013.01); *C12N 2799/022* (2013.01)

(58) Field of Classification Search
None
See application file for complete search history.

(56) References Cited

U.S. PATENT DOCUMENTS

| 7,807,784 B2 | 10/2010 | Fu | |
| 7,811,983 B2 * | 10/2010 | Fu | A61K 39/0011 424/184.1 |
| 8,263,081 B2 | 9/2012 | Fu | |
| 2002/0115110 A1 | 8/2002 | Brigham-Burke et al. | |
| 2005/0025754 A1 | 2/2005 | Fu | |
| 2007/0071675 A1 | 3/2007 | Wu et al. | |

FOREIGN PATENT DOCUMENTS

WO    WO 03/040307    5/2003

OTHER PUBLICATIONS

Ali et al., "The use of DNA viruses as vectors for gene therapy," Gene Therapy, 1: 367-384 (1994).
Anderson, "Human Gene Therapy," Science, 256 (5058): 808-813 (1992).
Armentano et al., "Effect of the E4 Region on the Persistence of Transgene Expression from Adenovirus Vectors," Journal of Virology: 71 (3), 2408-2416 (1997).
Bandyopadhyay et al., "Expression of a Complete Chicken Thymidine Kinase Gene Inserted in a Retrovirus Vector," Molecular and Cellular Biology, 4 (4): 749-754 (1984).
Berkner, "Expression of Heterologous Sequences in Adenoviral Vectors," Current Topics in Microbiology and Immunology, 158: 39-66 (1992).
Blank et al., "PD-L1/B7H-1 Inhibits the Effector Phase of Tumor Rejection by T Cell Receptor (TCR) Transgenic CD8+ T Cells," Cancer Research, 64: 1140-1145 (2004).
Boon et al., "Human Tumor Antigens Recognized by T Lymphocytes," J. Exp. Med., 183: 725-729 (1996).
Boyce et al., "Baculovirus-mediated gene transfer into mammalian cells," Proc. Natl. Acad. Sci. USA, 93: 2348-2352 (1996).
Cannon et al., "Induction of Transgene Expression in Tg.AC (v-Ha-ras) Transgenic Mice Concomitant with DNA Hypomethylation," Molecular Carcinogenesis, 21: 244-250 (1998).
Carter, CRC Handbook of Panoviruses, The Growth Cycle of Adeno-Associated Viruses, vol. 1, CRC Press, Boca Raton, FL, pp. 155-168 (1990).
Chen et al., "Costimulation of T cells for tumor immunity," Immunology Today, 14 (10): 483-486 (1993).
Chen et al., "Persistence in muscle of an adenoviral vector that lacks all viral genes," Proc. Natl. Acad. Sci. USA, 94: 1645-1650 (1997).
Cyster, "Chemokines and Cell Migration in Secondary Lymphoid Organs," Science, 286: 2098-2102 (1999).
Dougall et al., "RANK is essential for osteoclast and lymph node development," Genes Dev., 13: 2412-2424 (1999).
Engelhardt et al., "Prolonged Transgene Expression in Cotton Rat Lung with Recombinant Adenoviruses Defective in E2a," Human Gene Therapy, 5: 1217-1229 (1994).
Ettinger, "The Role of Tumor Necrosis Factor and Lymphotoxin in Lymphoid Organ Development," Current Topics in Microbiology and Immunology, 251: 203-210 (2000).
Fu et al., "Development and Maturation of Secondary Lymphoid Tissues," Annu. Rev. Immunol., 17: 399-433 (1999).
Goldstein et al., "Defective Lipoprotein Receptors and Atherosclerosis, Lessons from an Animal Counterpart of Familial Hypercholesterolemia," The New England Journal of Medicine, 309 (5): 288-296 (1983).
Hu et al., "Design of Retroviral Vectors and Helper Cells for Gene Therapy," Pharmacological Reviews, 52 (4): 493-511 (2000).
Ishibashi et al., "Hypercholesterolemia in Low Density Lipoprotein Receptor Knockout Mice and its Reversal by Adenovirus-mediated Gene Delivery," J. Clin. Invest., 92: 883-893 (1993).
Ishibashi et al., "Massive Xanthomatosis and Atherosclerosis in Cholesterol-fed Low Density Lipoprotein Receptor-negative Mice," J. Clin. Invest., 93: 1885-1893 (1994).

(Continued)

Primary Examiner — Laura B Goddard
(74) Attorney, Agent, or Firm — Casimir Jones SC; David Staple

(57) ABSTRACT

Antibody-LIGHT fusion products or conjugates stimulate immunity against tumors and eradicate metastases. Tumor-specific antibodies coupled with LIGHT effectively target metastatic tumors and reduces cancer metastases.

8 Claims, 6 Drawing Sheets

(56) References Cited

OTHER PUBLICATIONS

Jooss et al., "Cyclophosphamide Diminishes Inflammation and Prolongs Transgene Expression Following Delivery of Adenoviral Vectors to Mouse Liver and Lung," *Human Gene Therapy*, 7: 1555-1566 (1996).
Kang et al., "Signaling via LTβR on the lamina propria stromal cells of the gut is required for IgA production," *Nature Immunology*, 3 (6): 576-582 (2002).
Kay et al., "Transient immunomodulation with anti-CD40 ligand antibody and CTLA4Ig enhances persistence and secondary adenovirus-mediated gene transfer into mouse liver," *Proc. Natl. Acad. Sci. USA*, 94: 4686-4691 (1997).
Kay et al., "Viral vectors for gene therapy: the art of turning infectious agents into vehicles of therapeutics," *Nature Medicine*, 7 (1): 33-40 (2001).
Kim et al., "Regulation of Peripheral Lymph Node Genesis by the Tumor Necrosis Factor Family Member TRANCE," *J. Exp. Med.*, 192 (10): 1467-1478 (2000).
Kong et al., "Activated T cells regulate bone loss and joint destruction in adjuvant arthritis through osteoprotegerin ligand," *Nature*, 402: 304-309 (1999).
Kuriyama et al., "Pretreatment with Protease is a Useful Experimental Strategy for Enhancing Adenovirus-Mediated Cancer Gene Therapy," *Human Gene Therapy*, 11: 2219-2230 (2000).
Lauterlein et al., *Clinical Chem Lab Med.*, 49:877-883 (2011).
Leder et al., "v-Ha-ras transgene abrogates the initiation step in mouse skin tumorigenesis: Effects of phorbol esters and retinoic acid ," *Proc. Natl. Acad. Sci. USA*, 87 (23): 9178-9182 (1990).
Madzak et al., "Efficient in vivo encapsidation of a shuttle vector into pseudo-simian virus 40 virions using a shuttle virus as helper," *Journal of General Virology*, 73: 1533-1536 (1992).
Margolskee et al., "Epstein-Barr Virus Based Expression Vectors," *Current Topics in Microbiology and Immunology*, 158: 67-95 (1992).
Mauri et al., "LIGHT, a New Member of the TNF Superfamily, and Lymphotoxin α Are Ligands for Herpesvirus Entry Mediator," *Immunity*, 8: 21-30 (1998).
Melero et al., "Monoclonal antibodies against the 4-1BB T-cell activation molecule eradicate established tumors," *Nature Medicine*, 3 (6): 682-685 (1997).
Miller, "Human gene therapy comes of age," *Nature*, 357: 455-460 (1992).
Miller, "Retroviral Vectors," *Current Topics in Microbiology and Immunology*, 158: 1-24 (1992).
Moss, "Poxvirus Expression Vectors," *Current Topics in Microbiology and Immunology*, 158: 25-38 (1992).
Muzyczka, "Use of Adeno-Associated Virus as a General Transduction Vector for Mammalian Cells," *Current Topics in Microbiology and Immunology*, 158: 97-129 (1992).
Ochsenbein et al., "Roles of tumour localization, second signals and cross priming in cytotoxic T-cell Induction," *Nature*, 411: 1058-1064 (2001).
Ostrand-Rosenberg et al., "Cell-based vaccines for the stimulation of immunity to metastatic cancers," *Immunological Reviews*, 170: 101-114 (1999).
Peace et al., "Lysis of Ras Oncogene-transformed Cells by Specific Cytotoxic T Lymphocytes Elicited by Primary In Vitro Immunization with Mutated Ras Peptide," *J. Exp. Med.*, 179: 473-479 (1994).
Rooney et al., "The Lymphotoxin-β Receptor Is Necessary and Sufficient for LIGHT-mediated Apoptosis of Tumor Cells," *The Journal of Biological Chemistry*, 275 (19): 14307-14315 (2000).
Rosenberg, "Progress in human tumour immunology and immunotherapy," *Nature*, 411: 380-384 (2001).
Ruddle, "Lymphoid Neo-organogenesis, Lymphotoxin's Role in Inflammation and Development," *Immunologic Research*, 19 (2-3): 119-125 (1999).
Sarma et al., "Cytotoxic T Lymphocytes to an Unmutated Tumor Rejection Antigen P1A: Normal Development but Restrained Effector Function In Vivo," *J. Exp. Med.*, 189 (5): 811-820 (1999).
Schiedner et al., "Genomic DNA transfer with a high-capacity adenovirus vector results in improved in vivo gene expression and decreased toxicity," *Nature Genetics*, 18: 180-183 (1998).
Sha et al., "Selective expression of an antigen receptor on CD8-bearing T lymphocytes in transgenic mice," *Nature*, 335: 271-274 (1988).
Somia et al., "Gene Therapy: Trials and Tribulations," *Nature Reviews*, 1: 91-99 (2000).
Tamada et al., "Modulation of T-cell-mediated immunity in tumor and graft-versus-host disease models through the LIGHT c-stimulatory pathway," *Nature Medicine*, 6 (3): 283-289 (2000).
Tanzawa et al., "WHHL-Rabbit: A Low Density Lipoprotein Receptor-Deficient Animal Model for Familial Hypercholesterolemia," *Febs Letters*, 118 (1): 81-84 (1980).
van Beusechem et al., "Recombinant adenovirus vectors with knobless fibers for targeted gene transfer," *Gene Therapy*, 7: 1940-1946 (2000).
Wang et al., "The complementation of lymphotoxin deficiency with LIGHT, a newly discovered TNF family member, for the restoration of secondary lymphoid structure and function," *Eur. J. Immunol.*, 32: 1969-1979 (2002).
Wang et al., "The regulation of T cell homeostasis and autoimmunity by T cell-derived LIGHT," *J. Clin. Invest.*, 108 (12): 1771-1780 (2001).
Watanabe, "Serial Inbreeding of Rabbits with Hereditary Hyperlipidemia (WHHL-Rabbit), Incidence and Development of Atheroschlerosis and Xanthoma," *Atheroschlerosis*, 36: 261-268 (1980).
Wick et al., "Antigenic Cancer Cells Grow Progressively in Immune Hosts without Evidence for T Cell Exhaustion or Systemic Anergy," *J. Exp. Med.*, 186 (2): 229-238 (1997).
Wilson, "Vehicles for gene therapy," *Nature*, 365: 691-692 (1993).
Wu et al., "The Requirement of Membrane Lymphotoxin for the Presence of Dendritic Cells in Lymphoid Tissues," *J. Exp. Med.*, 190 (5): 629-638 (1999).
Ye et al., "Gene therapy for cancer using single chain Fv fragments specific for 4-1BB," *Nature Medicine*, 8 (4): 343-348 (2002).
Ye et al., "Modulation of LIGHT-HVEM Costimulation Prolongs Cardiac Allograft Survival," *J. Exp. Med.*, 195 (6): 795-800 (2002).
Yu et al., "Complementary Role of CD4+ T Cells and Secondary Lymphoid Tissues for Cross-presentation of Tumor Antigen to CD8+ T Cells," *J. Exp. Med.*, 197 (8): 985-995 (2003).
Yu et al., "Intratumor depletion of CD+4 cells unmasks tumor immunogenicity leading to the rejection of late-stage tumors," *The Journal of Experimental Medicine*, 201 (5): 779-791 (2005).
Zaczek et al., *Histol Histopathol.*, 20:1005-1015 (2005).
Zhai et al., "LIGHT, A Novel Ligand for Lymphotoxin β Receptor and TR2/HVEM Induces Apoptosis and Suppresses in Vivo Tumor Formation Via Gene Transfer," *J. Clin. Invest.*, 102 (6): 1142-151 (1998).
Zimmerman et al., *Drug Discovery Today*, 12: 34-42 (Jan. 2007).
Zinkernagel, "Immunity Against Solid Tumors?," *Int. J. Cancer*, 93: 1-5 (2001).

* cited by examiner

ANTIBODY-LIGHT FUSION PRODUCTS FOR CANCER THERAPEUTICS

This application is a Divisional of copending U.S. patent application Ser. No. 13/563,372, filed Jul. 31, 2012, which is a Divisional of U.S. patent application Ser. No. 12/599,946, filed Dec. 30, 2009 (now U.S. Pat. No. 8,263,081), which is a U.S. nationalization under 35 U.S.C. §371 of International Application No. PCT/US2008/006381, filed May 14, 2008, which claims the benefit of priority under 35 U.S.C. §119(e) to U.S. Provisional Application No. 60/917,852, filed May 14, 2007. The disclosures set forth in the referenced applications are incorporated herein by reference in their entireties.

BACKGROUND

Methods and compositions are disclosed to target tumor cells with the LIGHT protein linked to a tumor antigen. The targeting reduces tumor growth and reduces metastases.

The paucity of activated T cells infiltrating established tumors in immunocompetent hosts helps to explain the inability of hosts to dispose of tumors. Experiments in animal models as well as clinical studies indicate that the immune system can recognize and kill individual tumor cells, but a host cannot generally eradicate established solid tumors. There may be several explanations for the failure of the host to respond effectively to established tumors: 1) lack of early T cell priming due to poor direct or indirect presentation in lymphoid tissues because of an inadequate number of tumor cells (especially those of non-hemopoietic origin) migrating to the lymphoid tissue; 2) inadequate numbers of immune cells migrating to tumor sites due to biological barriers around tumor tissues; 3) exhausted or short-lived activated antigen-specific T cells that fail to combat tumor growth due to limited repertoires; 4) unresponsiveness or ignorance of T cells to tumors; 5) an inhibitory microenvironment or lack of stimulation inside tumors to activate the immune system.

Clinically, an increase in the infiltration of T cells to the tumor site is closely associated with better prognosis. Previous studies have shown that preventive vaccinations were effective in inducing the rejection of inoculated tumor cells. After tumor growth has been established, however, therapeutic vaccinations usually fail to reject tumors. Surgical reduction of tumor does not boost the immune response to tumors. Furthermore, it was reported that even the expression of a strong antigen on tumor cells was insufficient in promoting the rejection of an established tumor, despite the presence of excessive numbers of antigen-specific T cells in the lymphoid tissues. Lack of T cells priming and/or infiltrating an established tumor is one of the major obstacles for either natural or therapeutic approaches against antigenic cancers. In addition, insufficient expression of costimulatory molecules inside tumor tissues may fail to activate infiltrating T cells and result in the anergy of tumor-reactive T cells.

The lack of early T cell priming is possibly attributed to only a few tumor cells that migrated from solid tissue to lymphoid tissues for direct presentation. Genetic analysis using bone marrow chimeras has revealed two modes of antigen presentation for priming MHC-I-restricted CD8+ T cells. Direct-priming is mediated by the engagement of T cells with the cells that synthesize the protein with antigenic epitopes, whereas cross-priming is mediated by the host antigen-presenting cells that take up antigens synthesized by other cells. The mechanisms for priming tumor-specific T cells has been vigorously debated and so far remains inconclusive. Understanding how and where tumor antigens are presented to T cells would help find a therapeutic action against tumors.

LIGHT (homologous to lymphotoxin, exhibits inducible expression, and competes with HSV glycoprotein D for herpes virus entry mediator, a receptor expressed by T lymphocytes) is a recently identified type II transmembrane glycoprotein of the TNF ligand superfamily. LIGHT (TNFSF14) is a tumor-necrosis factor (TNF) family member that interacts with Lymphotoxin β receptor (LTβR) and herpes virus entry mediator (HVEM) mainly expressed on stromal cells and T cells, respectively. LTβR signaling is required for the formation of organized lymphoid structures, which can be attributed, at least in part, to its ability to induce the expression of chemokines and adhesion molecules that attract naïve T cells and dendritic cells (DC) in lymphoid organs. Stimulation of LTβR on stromal cells by LIGHT in vivo leads to the expression of CCL21, which attracts naïve T cells in the T cell area of the spleen in the absence of LTαβ, another ligand for LTβR. These results demonstrate that LIGHT is able to interact with LTβR to regulate CCL21 chemokine expression. In addition, LIGHT exhibits a potent, CD28-independent co-stimulatory activity for T cell priming and expansion leading to enhanced T cell immunity against tumors and/or increased autoimmunity. Signaling via LTβR is required for the formation of organized lymphoid tissues. Lymphotoxin β receptor (LTβR) plays an important role in the formation of lymphoid structures. LTβR is activated by two members of the TNF family, membrane lymphotoxin αβ and LIGHT. LTβR plays pivotal roles in the formation of lymph nodes (LNs) and the distinct organization of T, B zones in secondary lymphoid organs. Signaling via LTβR regulates the expression of chemokines and adhesion molecules within secondary lymphoid organs. Chemokines and adhesion molecules control the migration and positioning of DCs and lymphocytes in the spleen. Over-expression of soluble LT or TNF in non-lymphoid tissues was sufficient to promote functional lymphoid neogenesis.

LIGHT has also been called HVEM-L and LT-γ. Under the new TNF nomenclature, it is called TNFSF14. LIGHT is a 240 amino acid (aa) protein that contains a 37 aa cytoplasmic domain, a 22 aa transmembrane region, and a 181 aa extracellular domain. Similar to other TNF ligand family members, LIGHT is predicted to assemble as a homotrimer. LIGHT is produced by activated T cells and was first identified by its ability to compete with HSV glycoprotein D for HVEM binding. LIGHT has also been shown to bind to the lymphotoxin beta receptor (LTβR) and the decoy receptor (DcR3/TR6).

LIGHT plays a unique role in T cell activation and the formation of lymphoid tissue. Interactions between LIGHT and LTβR restore lymphoid structures in the spleen of LTα$^{-/-}$ mice. In addition, the upregulation of LIGHT causes T cell activation and migration into non-lymphoid tissues providing for the formation of lymphoid-like structures. Conversely, LIGHT$^{-/-}$ mice showed impaired T cell activation and delayed cardiac rejection. Therefore, LIGHT is a potent costimulatory molecule that also promotes the formation of lymphoid tissues to enhance local immune responses. Lack of efficient priming of naïve T cells in draining lymphoid tissues and the inability to expand tumor-specific T cells within tumors prevent the eradication of cancer.

Micrometastases (small aggregates of cancer cells visible microscopically) can become established at a very early stage in the development of heterogeneous primary tumors and seed distal tissue sites prior to their clinical detection. For example, the detectable metastasis in breast cancer can be observed when the primary tumor size is very small. Therefore, at the time of diagnosis, many cancer patients already have microscopic metastasis, an observation that has led to the development of post-surgical adjuvant therapy for patients with solid tumors. Despite these advances, success has been limited, and optimal treatment of metastatic disease continues to pose a significant challenge in cancer therapy.

A variety of human and murine cancers have been proven to be antigenic and able to be recognized by T cells. Tumor-reactive T cells could theoretically seek out and destroy tumor antigen-positive cancer cells and spare the surrounding healthy tissues. However, the naturally existing T cell responses against malignancies in human are often not sufficient to cause regression of the tumors, primary or metastases. It has been recently reported that sporadic spontaneous, but immunogenic tumors avoid destruction by inducing T cell tolerance. However, the activation of tumor antigen-specific T cells may completely prevent the development of spontaneous tumors. Thus, breaking tolerance and generating such T cells capable of rejecting tumors around the time of treatment of the primary tumor could represent a potential approach to clearing metastatic tumor cells. As antigen-lost variants can escape under immunological pressure, immunotherapy should be applicable independent of knowledge of specific tumor antigens.

From an immunological perspective, present clinical strategies hinder the immune defense against malignancies and further diminish the effectiveness of immunotherapy. Although removal of a tumor may reverse tumor-induced immune suppression, surgical excision of the primary tumor before immunotherapy also removes the major source of antigen, which may lead to a reduction of the activation of cytotoxic T-lymphocytes (CTL) since the efficiency of priming is correlated with the tumor antigen load. In addition, current adjuvant treatments, which include chemotherapy and radiation therapy, that are meant to kill residual tumor cells may in fact impair anti-tumor immune responses by destroying or inhibiting T cells.

Metastatic disease is the major cause of morbidity and mortality in cancer. While surgery, chemotherapy, or radiation can often control primary tumor growth, successful eradication of disseminated metastases remains rare. One unsolved problem is whether such response allows incoming CTL to be educated and then exit the tumor site. Another unsolved problem is whether these CTL can then patrol and effectively eliminate spontaneously metastasized tumor cells in the periphery. Local treatment of tumor with LIGHT generates plenty of tumor specific CTL that exit the primary tumor and infiltrate distal tumors to completely eradicate preexisting spontaneous metastases.

As indicated above, the naturally occurring T cell responses against malignancies in humans are often not sufficient to cause regression of tumors, primary or metastatic. Immunotherapy would potentially elicit tumor-reactive T cells that can seek and destroy disseminated tumor antigen-positive cancer cells while sparing the surrounding healthy tissues, but active vaccination for tumor bearing host only shows limited benefit. Lack of well-defined antigens in most tumors limits either active vaccination or adoptive transfer therapy. Immunotherapy that is effective even without determination of specific tumor antigens would be more applicable and more therapeutically feasible. However, it is still unclear when and how to boost active immune responses against tumor tissues.

Naïve or effector-memory T cells can leave the periphery and enter the draining lymph nodes through an active process. It is not yet known if sufficient number of tumor-specific CTLs recruited to the primary tumor can survive and exit the microenvironment to patrol peripheral tissues and eradicate disseminated metastases. In addition, a challenge in developing an effective immunotherapy is to devise an approach to increase the number of or enhance the function of circulating tumor-specific T cells that may detect and destroy microscopic metastatic cells before they become clinically meaningful. The delivery of LIGHT, using a recombinant adenovirus, into the primary tumor can help generate CTL which can then exit out of the local tumor and patrol periphery tissue to eradicate metastases before they are clinically meaningful.

In the present disclosure targeting tumors with antibody-LIGHT fusion/conjugate products or linked products generate strong immunity against primary tumor and metastases.

SUMMARY

Targeting tumor cells with LIGHT protein or a peptide fragment thereof linked to an antibody against a tumor antigen reduces the growth of tumors and also reduces metastasis including micro-metastasis. Further, cytokines linked to an antibody against tumor antigens are useful against micrometastasis.

Inducing an immune response in tumor tissues via an antibody-LIGHT fusion or conjugated composition prior to surgery generates sufficient primed antigen-specific effector T cells that exit the tumor and eradicate metastasis. An antibody specific to a cancer antigen and LIGHT that is resistant to protease digestion (e.g., mutant LIGHT) can also be administered separately. Targeting the primary tumor with TNFSF14 (LIGHT) prior to surgical excision is a new strategy to elicit better immune response for the eradication of spontaneous metastases. Antibody-LIGHT treatment slows down the growth of aggressive tumor.

A composition includes a tumor specific antibody linked to a fragment of a human LIGHT protein, wherein the LIGHT fragment is resistant to protease digestion in a tumor environment and is sufficient to stimulate cytotoxic T lymphocytes against tumor cells.

A composition includes a tumor specific antibody linked to a fragment of a LIGHT protein. The antibody and the fragment of the LIGHT protein may form a fusion protein, or the fragment of the LIGHT protein may be chemically conjugated or linked otherwise to the antibody or a fragment of the antibody.

Any peptide fragment derived from LIGHT protein including recombinant peptides, synthetic peptides, recombinant LIGHT protein, mutant LIGHT protein, truncated LIGHT protein, extracellular domain of LIGHT, conserved domains of LIGHT, peptide mimetics that resemble a LIGHT domain, LIGHT protein or peptides thereof with modified amino acids are suitable for use in inducing immune response by linking or conjugating of fusing to a tumor specific agent, such as, for example, an antibody or a fragment thereof, provided the LIGHT fragment is capable of being stably present on a tumor cell surface.

A composition includes a humanized monoclonal antibody or a chimeric antibody or a heterominibody or a single chain antibody.

An antibody fragment used in conjunction with LIGHT is sufficient to recognize a tumor antigen. The fragment is sufficient to stimulate cytotoxic T lymphocytes.

A fragment of LIGHT may include about 100-150 amino acids of LIGHT. A fragment of LIGHT may an amino acid sequence from positions about 85-240 of LIGHT. A fragment of LIGHT may also include about 100-150 amino acids of LIGHT. A fragment of LIGHT may include an amino acid sequence from positions about 90-240 of LIGHT. A fragment of LIGHT may include an amino acid sequence from positions about 84-240 or 83-240 or 82-240 of LIGHT.

A fragment of LIGHT may also include about 100-150 amino acids of LIGHT, provided the fragment is capable of inducing immune response against tumor cells. A fragment of LIGHT may include an amino acid sequence from positions about 90-235 of LIGHT.

A fragment of LIGHT is a protease resistant fragment. A fragment of LIGHT may include a mutation in a protease recognition sequence EQLI (Residues 81-84 of SEQ ID NO: 1).

A composition is disclosed wherein the LIGHT fragment includes an extracellular domain with an amino acid sequence:

```
                                           (SEQ ID NO: 2)
QLHWRLGEMVTRLPDGPAGSWEQLIQERRSHEVNPAAHLTGANSSLTGSG

GPLLWETQLGLAFLRGLSYHDGALVVTKAGYYYIYSKVQLGGVGCPLGLA

STITHGLYKRTPRYPEELELLVSQQSPCGRATSSSRVWWDSSFLGGVVHL

EAGEKVVVRVLDERLVRLRDGTRSYFGAFMV.
```

A method of reducing the growth of primary tumor and/or cancer metastasis, includes the steps of:
administering a pharmaceutical composition comprising a tumor-specific antibody linked to a LIGHT polypeptide fragment; and
reducing the growth of primary tumor and/or cancer metastasis by stimulating activation of tumor-specific T-cells against the tumor.

The antibody recognizes a surface tumor antigen and the antibody may be conjugated to the LIGHT fragment chemically or recombinantly fused or linked otherwise to the LIGHT fragment.

The pharmaceutical composition including the antibody-LIGHT may be administered intravenously.

Cancer metastasis may be reduced by stimulation of at least one of the following including chemokines, adhesion molecules, and costimulatory molecules for priming naïve T-cells. Cancer types include breast cancer, lung cancer, prostrate cancer, colon cancer, and skin cancer.

A method of reducing the growth of primary tumor and/or cancer metastasis, includes the steps of:
(a) administering a pharmaceutical composition comprising a tumor-specific antibody linked to a LIGHT polypeptide fragment;
(b) introducing a nucleic acid molecule encoding LIGHT or a fragment thereof into an individual at a tumor site, wherein the LIGHT is protease resistant; and
(c) reducing the growth of primary tumor cancer metastasis by stimulating activation of tumor-specific T-cells against the tumor.

The nucleic acid may be delivered to a pre-existing tumor site or that the nucleic acid is delivered to a site distal to a pre-existing tumor site.

A chemotherapeutic agent may also be administered during or prior to or after an antibody-LIGHT therapy.

Radiotherapy may also be administered during or prior to or after an antibody-LIGHT therapy.

Embodiments of the antibody is specific to a tumor antigen may be selected from the group consisting of HER2, HER4, HER8, STEAP, and EGFR and any other anti-cancer antigen.

A method of reducing the growth of primary tumor and/or cancer metastasis, includes the steps of:
(a) administering a pharmaceutical composition comprising a tumor-specific antibody;
(b) introducing a nucleic acid molecule encoding a LIGHT protein or a fragment thereof at a tumor site, wherein the LIGHT is protease resistant;
(c) expressing the LIGHT protein or a fragment thereof on the surface of a tumor cell; and
(d) reducing the growth of the tumor and/or cancer metastasis by stimulating activation of tumor-specific T-cells against the tumor.

A chimeric protein including a peptide region that recognizes a tumor antigen and a fragment of a LIGHT protein is disclosed. The agent may be a ligand that binds a tumor surface receptor.

A composition is described including a fragment of a LIGHT protein and an agent that specifically recognizes a tumor cell.

A pharmaceutical composition including a LIGHT peptide fragment coupled with a tumor specific component. The tumor specific component may include a ligand to a receptor in a tumor cell surface or a receptor that recognizes a ligand on tumor cell surface.

A novel method to treat tumors (solid tumors in particular) is to create lymphoid-like microenvironments that express chemokines, adhesion molecules, and costimulatory molecules required for priming naïve T cells and expanding activated T cells by the use of mutant LIGHT molecules. Broader T cells are generated against tumors. Direct delivery of antibody-LIGHT fusion or conjugates are effective against tumors and metastasis. Tumor volume is reduced in vivo when antibody-LIGHT conjugates or fusion products are targeted to tumors as compared to tumors treated with controls.

In various embodiments, the mutant LIGHT has an amino acid change in a proteolytic site including an amino acid sequence EQLI (Residues 81-84 of SEQ ID NO: 1) from positions 81-84 of native LIGHT protein. In an embodiment, the mutant LIGHT does not have the proteolytic site, an amino acid sequence EQLI (Residues 81-84 of SEQ ID NO: 1) from positions 81-84 of native LIGHT protein.

The nucleic acid molecule disclosed encodes a recombinant LIGHT including an extracellular domain:

```
                                           (SEQ ID NO: 2)
QLHWRLGEMVTRLPDGPAGSWEQLIQERRSHEVNPAAHLTGANSSLTGSG

GPLLWETQLGLAFLRGLSYHDGALVVTKAGYYYIYSKVQLGGVGCPLGLA

STITHGLYKRTPRYPEELELLVSQQSPCGRATSSSRVWWDSSFLGGVVHL

EAGEKVVVRVLDERLVRLRDGTRSYFGAFMV.
```

Cancer metastasis is reduced by stimulation of cytotoxic T-lymphocytes, and/or by stimulation of chemokines, adhesion molecules, and costimulatory molecules for priming naïve T-cells. T-cells are activated within a tumor site, and may circulate in blood. Circulating T-cells are preferably cancer specific. The T-cell generation may be CD8+ dependent.

An isolated recombinant nucleic acid includes a nucleotide sequence encoding a protease digestion resistant mutant LIGHT. An embodiment of the nucleotide sequence is:

(SEQ ID NO: 3)
ATGGAGGAGAGTGTCGTACGGCCCTCAGTGTTTGTGGTGGATGGACAGAC

CGACATCCCATTCACGAGGCTGGGACGAAGCCACCGGAGACAGTCGTGCA

GTGTGGCCCGGGTGGGTCTGGGTCTCTTGCTGTTGCTGATGGGGCTGGG

CTGGCCGTCCAAGGCTGGTTCCTCCTGCAGCTGCACTGGCGTCTAGGAGA

GATGGTCACCCGCCTGCCTGACGGACCTGCAGGCTCCTGGGAGCAGCTGA

TACAAGAGCGAAGGTCTCACGAGGTCAACCCAGCAGCGCATCTCACAGGG

GCCAACTCCAGCTTGACCGGCAGCGGGGGCCGCTGTTATGGGAGACTCA

GCTGGGCCTGGCCTTCCTGAGGGGCCTCAGCTACCACGATGGGGCCCTTG

TGGTCACCAAAGCTGGCTACTACTACATCTACTCCAAGGTGCAGCTGGGC

GGTGTGGGCTGCCCGCTGGGCCTGGCCAGCACCATCACCCACGGCCTCA

CAAGCGCACACCCCGCTACCCCGAGGAGCTGGAGCTGTTGGTCAGCCAGC

AGTCACCCTGCGGACGGGCCACCAGCAGCTCCCGGGTCTGGTGGGACAGC

AGCTTCCTGGGTGGTGTGGTACACCTGGAGGCTGGGGAGAAGGTGGTCGT

CCGTGTGCTGGATGAACGCCTGGTTCGACTGCGTGATGGTACCCGGTCTT

ACTTCGGGGCTTTCATGGTGTGA, wherein the sequence encoding the protease digestion site
GAGCAGCTGATA (Residues 241-252 of SEQ ID NO: 3)
is mutated.

DETAILED DESCRIPTION

Figure 1:
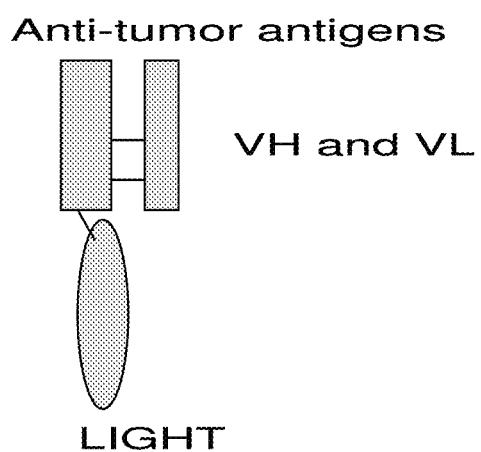
FIG. 1 shows schematic illustrations of the AG 104A tumor specific heterodireic constructs. Human Cκ was fused via the flexible upper hinge region of human IgG3 to the C-terminus of a scFv-fragment that was derived from a cancer antigen.

Metastatic disease is a major cause of mortality among cancer patients. Initial dormancy of metastasis or small primary tumors may be attributed to the insufficient levels of antigens available to prime CD8+ T cells. Therapeutic methods that utilize an antibody recognizing an antigen expressed by tumor cells coupled with LIGHT (antibody-LIGHT) specifically and effectively target migrant tumor cells after such Antibody-LIGHT is introduced systemically by intravenous (i.v.) injection.

As an example, in a mouse model, a high-affinity monoclonal antibody against tumor cells accumulates inside tumors in vivo with high concentration after intravenous injection. The heterominibody LIGHT (by conjugation or genetic linkage) allows LIGHT to be specifically delivered into tumor tissue at various distal sites after its systemic introduction.

A LIGHT fusion protein (e.g., antibody-LIGHT couple) selectively accumulates inside tumor tissues and specifically binds to tumors in vitro.

Therapeutic methods that utilize an antibody recognizing an antigen expressed by tumor cells coupled with LIGHT (antibody-LIGHT) are designed to specifically and effectively target migrant tumor cells after the Antibody-LIGHT is introduced systemically by intravenous injection. Any tumor antigen that is expressed on the surface of the tumor cell or is capable of being recognized by a tumor-specific antibody is suitable to be coupled with LIGHT or a functional fragment thereof.

Local delivery of a protease resistant LIGHT (e.g., a mutant LIGHT or an extracellular domain of LIGHT) enhances direct presentation of tumor antigens to antigen-specific T cells and prevents anergy of infiltrated T cells within the tumor microenvironment. In addition, LIGHT may enhance tumor apoptosis in vivo.

Successful eradication of metastasis by currently available cancer treatments remains rare. Generating immune responses in primary tumor tissues prior to surgical resection produces tumor-specific effector T cells sufficient to eradicate distant metastases. Priming of tumor-specific CD8+ T cells, for example by antibody-LIGHT delivery in the primary tumor promotes subsequent exit of cytotoxic T lymphocytes (CTL) that home to distal tumors. Targeting primary tumor prior to surgical excision elicits immune-mediated eradication of spontaneous metastasis.

Metastasis is often a fatal step in the progression of solid malignancies. Disseminated metastatic tumor cells can remain dormant and clinically undetectable for months or even years following surgical resection of the primary tumor, leading to subsequent clinical disease recurrence. Immunotherapeutic strategies are suitable to eliminate this micrometastatic disease. As an example, delivery of antibody-LIGHT into the primary tumor reduces the formation of metastasis and rejects the established metastasis in peripheral tissues. For example, direct delivery of LIGHT in the form of an antibody-LIGHT fusion protein to tumors (e.g., primary tumor) generates sufficient number of effector/memory T cells from the tumor tissues that move to a distal site, leading to an overall increase in the intensity of the immune response, greater inflammatory cytokine production, and the eradication of spontaneous metastasis. Immunotherapy using primary tumor tissues aimed to provoke and sustain a tumor specific immune response in the presence of endogenous tumor antigens generates the necessary CTL to clear already disseminated tumor cells.

In the presence of LIGHT on the surface of a tumor, CTLs are efficiently primed and subsequently circulate to infiltrate LIGHT-negative distal tumors. Without the benefits of LIGHT being present in the primary tumor, few activated T cells are expected at a secondary tumor site. It is likely that these effector/memory T cells generated in the local tumor site in the presence of LIGHT are able to exit the tumor and patrol the periphery and identify metastatic tumor cells. Chemokine receptor (CCR7) has been recently shown to be a key molecule for T cells to exit the peripheral tissues, including the inflammatory site, and traffic to the draining LN. The 2C T cells exiting LIGHT-expressing tumors may be controlled by CCR7.

Figure 2:
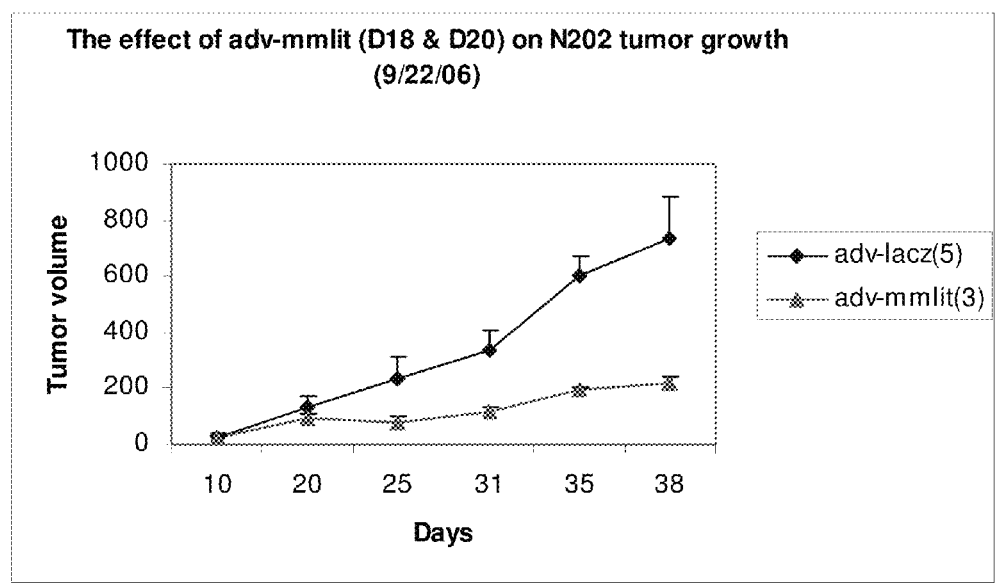
FIG. 2 demonstrates that Adv-mmlit inhibits neu+ N202 tumor growth. About $8 \times 10^5$ N202 1A cells were injected (i.c.). Intratumoral injections of about $2 \times 10^{10}$ vp adv-lacz or adv-mmlit were performed at day 18 and day 20. The size of tumor was monitored twice a week.
Figure 3:
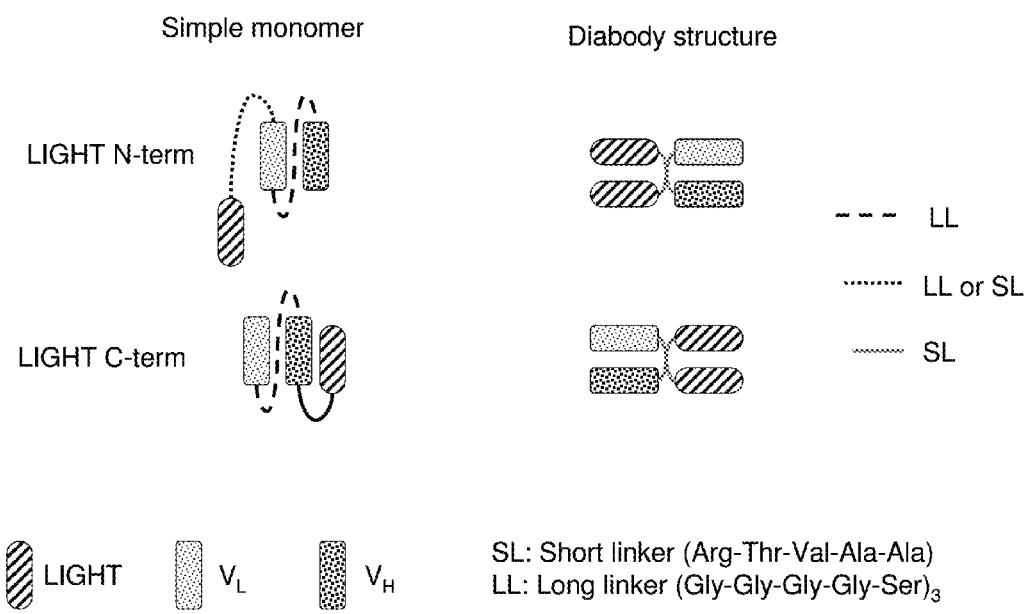
FIG. 3 shows scFv-LIGHT fusion protein structure design. The short linker sequence is disclosed as SEQ ID NO: 11 and the long linker sequence is disclosed as SEQ ID NO: 12.

For example, an extracellular domain of LIGHT molecule can be recombinantly expressed such that either the recombinant form does not have the proteolytic site all together or has one or more amino acid changes that renders the recombinant form protease digestion resistant (mutant LIGHT). In addition, the extracellular domain or a functional equivalent derivative of the extracellular domain of LIGHT can be linked to a tether or linker or spacer sequence to anchor the extracellular domain in the membrane of tumor cells. FIGS. 2-3 illustrate some aspects of an antibody-LIGHT fusion or conjugation.

The extracellular domain of LIGHT refers to a form of the LIGHT polypeptide which is essentially free of the transmembrane and cytoplasmic domains. The extracellular domain of LIGHT has less than 1% of such transmembrane and/or cytoplasmic domains and preferably, will have less than 0.5% of such domains. It is to be understood that any transmembrane domains identified for the LIGHT polypeptides are identified pursuant to criteria routinely employed in the art for identifying that type of hydrophobic domain. The exact boundaries of a transmembrane domain may vary but most likely by no more than about 2-5 amino acids at either end of the domain as initially identified herein. An extracellular domain of a LIGHT polypeptide may contain from about 5 or fewer amino acids on either side of the transmembrane domain/extracellular domain boundary as identified herein.

Suitable LIGHT protein fragments and peptides thereof include for example, amino acid positions 1-240 of LIGHT without one or more of the amino acids representing the proteolytic site EQLI (Residues 81-84 of SEQ ID NO: 1) (81-84); amino acid positions 1-240 of LIGHT with one or more of the amino acids representing the proteolytic site EQLI (Residues 81-84 of SEQ ID NO: 1) (81-84) is mutated or otherwise inactivate; 82-240 of LIGHT; 83-240 of LIGHT; 84-240 of LIGHT; 85-240 of LIGHT; 90-240 of LIGHT; 95-240 of LIGHT; 100-240 of LIGHT; 85-235 of LIGHT; 85-230 of LIGHT; 85-225 of LIGHT; 85-220 of LIGHT; 85-215 of LIGHT; 85-200 of LIGHT; LIGHT fragment without the intracellular and membrane domain; and any fragment that is about 100-150 amino acids in length of LIGHT that is resistant to protease digestion.

"Antibody-LIGHT" refer to an antibody or a fragment thereof specific against a tumor antigen, which is either fused or conjugated to a fragment of LIGHT protein that is sufficient to trigger an immune response against tumor cells and is capable of being stably present on a tumor cell surface by being resistant to protease digestion compared to a native LIGHT protein.

As used herein, the term "LIGHT" in an antibody-LIGHT couple refers to either an extracellular domain of LIGHT that does not contain a protease recognition sequence, or a mutant LIGHT wherein the protease site (EQLI (Residues 81-84 of SEQ ID NO: 1)) is inactivated by entire deletion or a mutation at one or more amino acids that render the protease site insensitive or inactive or a truncated form of LIGHT that is resistant to protease digestion and capable of stimulating T-cells.

"Mutant LIGHT" refers to a LIGHT protein or a LIGHT-derived peptide that is resistant to proteolytic cleavage, capable of being stably expressed in the surface of tumor cells, and exhibits increased activation of tumor specific T-cells, compared to normal or native LIGHT protein. The "mutant LIGHT" relates to a LIGHT protein or LIGHT protein-derived peptides or fragments that are resistant to protease digestion or otherwise are capable of being stably expressed on the surface of cells including tumor cells because of a mutation that renders the proteolytic site EQLI (Residues 81-84 of SEQ ID NO: 1) inactive. There are several ways to generate mutant LIGHT. For example, the protease site (e.g., EQLI (Residues 81-84 of SEQ ID NO: 1)) can be mutated either to remove the protease site in toto or to render the site resistant to protease digestion by changing (e.g., insertion, deletion, substitution) one or more amino acids at the protease site.

"Truncated LIGHT" protein refers to a LIGHT fragment that is not full length when compared to a native LIGHT, is resistant to protease digestion and is capable of stimulating T-cells against tumor cells. For example, the extracellular domain of LIGHT (about 85-240) is a suitable truncated LIGHT. Truncated LIGHT includes fragments/derivatives of LIGHT protein that are resistant to protease digestion thereby exhibiting the ability to be present on the cell surface for an extended period of time compared to native LIGHT protein.

To generate protease resistant LIGHT protein (e.g., mutant LIGHT) or fragments or LIGHT protein or LIGHT peptides with the protease site inactivated, for example, the amino acid glutamic acid (E), can be deleted or substituted within the protease recognition sequence EQLI (Residues 81-84 OF SEQ ID NO: 1). Similarly, the amino acid glutamine (Q) is deleted or substituted with another amino acid within the protease recognition sequence EQLI (Residues 81-84 OF SEQ ID NO: 1). Similarly, amino acid L or I can be deleted or substituted with other amino acids. Protease resistant amino acid analogs can also be used to generate synthetic LIGHT fragments that protease resistant. For example, using the incorporation of β-amino acids into peptides decreases proteolysis and can be used to substitute the protease sensitive site EQLI (Residues 81-84 OF SEQ ID NO: 1). Rational incorporation of β-amino acids within the protease site and near the protease site can be performed and the resulting mutants tested for protease resistance. A variety of techniques including site directed mutagenesis can be used to generate LIGHT fragments that are resistant to protease digestion.

The term "inactivated" means that the LIGHT protein or its fragments thereof is resistant to protease digestion in a tumor environment because the protease recognition site has been selectively silenced either by mutation in one or more amino acids or by deletion of EQLI (Residues 81-84 OF SEQ ID NO: 1) or by substitution of one or more amino acids with α- or β-amino acids or by any suitable way.

The term "resistant" means that the LIGHT protein or its fragments thereof is not sensitive to protease digestion in a tumor environment because the protease recognition site has been inactivated/mutated either by mutation in one or more amino acids or by deletion of EQLI (Residues 81-84 OF SEQ ID NO: 1) or by substitution of one or more amino acids with α- or β-amino acids or by any suitable way.

The term "tumor environment" refers to the presence and expression and activity of cellular proteases including extracellular proteases that may co-operatively influence matrix degradation and tumor cell invasion through proteolytic cascades, with individual proteases having distinct roles in tumor growth, invasion, migration, angiogenesis, metastasis and expansion of tumors.

"Ad-LIGHT" or "Ad-mutant LIGHT" refers to recombinant adenoviral vector system that contains mutant LIGHT encoding nucleic acids and is suitable for delivering the nucleic acid sequences to a tumor site or capable of infecting tumor cells.

"Metastasis or metastases" refers to the process by which cancer spreads from the location at which the cancer initiated as a tumor to one or more distant locations in the body by migration of one or more cancerous cells. These terms also include micro-metastasis wherein the formation of tumors at distal locations correspond to small aggregates of cancer cells that are visible microscopically. These terms also refer to the secondary cancerous growth resulting from the spread of the primary tumor from the original location.

"Reducing or controlling metastasis" refers to a reduction in the number of metastatic tumor sites as compared to a control.

"Adoptive transfer" refers to the transfer of T cells into recipients.

"Tumor site" means a location in vivo or ex vivo that contains or is suspected of containing tumor cells. Tumor site includes solid tumors and also the locations that are adjacent or immediately near a tumor growth.

"Tumor-specific" refers to antibody or any other ligand/receptor that shows preference to tumor cells over normal cells. For example, an antibody targeted to an antigen present on tumor cells is considered tumor-specific. A tumor-specific antibody may also bind to a normal cell if the target antigen is present, albeit to a lesser degree.

As used herein, the term "administration" refers to systemic and/or local administration. The term "systemic administration" refers to non-localized administration such that an administered substance may affect several organs or tissues throughout the body or such that an administered substance may traverse several organs or tissues throughout the body in reaching a target site. For example, administration into a subject's circulation may result in expression of a therapeutic product from an administered vector in more than one tissue or organ, or may result in expression of a therapeutic product from an administered vector at a specific site, e.g., due to natural tropism or operable linkage of tissue-specific promoter elements. One of skill in the art would understand that various forms of administration are encompassed by systemic administration, including those forms of administration encompassed by parenteral administration such as intravenous, intramuscular, intraperitoneal, and subcutaneous administration. In some embodiments, systemic administration can be used to elicit a systemic effect associated with treatment of a local or systemic disease or condition. A systemic effect may be desirable for a local disease or condition, for example, to prevent spread of said disease or condition. The term "local administration" refers to administration at or near a specific site. One of skill in the art would understand that various forms of administration are encompassed by local administration, such as direct injection into or near a specific site. In some embodiments, local administration is associated with treatment of a disease or condition where a local effect is desired (e.g. administration to the lung for the treatment of lung cancer). A local effect may be desired in association with either local or systemic diseases or conditions. A local effect may be desired in association with a systemic disease or condition to treat a local aspect of a systemic disease or condition.

An "effective amount" Antibody-LIGHT fusion product or conjugate refers to an amount sufficient to carry out a specifically stated purpose. An "effective amount" may be determined empirically and in a routine manner, in relation to the stated purpose. A suitable purpose for the Antibody-LIGHT couple is reduce tumor size or growth and/or reduce metastases.

The term "therapeutically effective amount" refers to an amount of an antibody conjugate or fusion product of LIGHT polypeptide effective to treat a disease or disorder in a subject or mammal. In the case of cancer, the therapeutically effective amount of the compositions disclosed herein may reduce the number of cancer cells; reduce the tumor size; inhibit (i.e., slow and/or stop) cancer cell infiltration into peripheral organs; inhibit (i.e., slow and/or stop) tumor metastasis; inhibit tumor growth; and/or relieve one or more of the symptoms associated with the cancer.

The term "antibody" covers, for example, monoclonal antibodies, polyclonal antibodies, single chain antibodies, fragments of antibodies (see below) as long as they exhibit the desired biological or immunological activity. The term "immunoglobulin" (Ig) is used interchangeable with antibody herein. The antibodies may specifically target a tumor antigen, e.g., surface tumor antigen such as for example Her2/neu and CD20.

An "isolated antibody" is one which has been identified and separated and/or recovered from a component of its natural environment. The antibody is purified to greater than 95% by weight of antibody as determined by the Lowry method, and more than 99% by weight.

The term "monoclonal antibody" as used herein refers to an antibody obtained from a population of substantially homogeneous antibodies, i.e., the individual antibodies of the population are identical except for possible naturally occurring mutations that may be present in minor amounts. Monoclonal antibodies are highly specific, being directed against a single antigenic site or an epitope. For example, the monoclonal antibodies may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate, and human constant region sequences.

"Antibody fragments" include a portion of an intact antibody, for example the antigen binding or variable region of the intact antibody. Examples of antibody fragments include Fab, Fab', F(ab')$_2$, single chain F$_v$ and F$_v$ fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may include residues that are not found in the recipient antibody or in the donor antibody. These modifications are made to further refine antibody performance. In general, the humanized antibody includes substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also includes at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be performed following the method of Winter and co-workers [Jones et al., Nature, 321:522-525 (1986); Riechmann et al., Nature, 332:323-327 (1988); Verhoeyen et al., Science, 239: 1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Various forms of a humanized antibody-LIGHT fusions or conjugates are contemplated. For example, the humanized antibody may be an antibody fragment, such as a Fab, which is conjugated with LIGHT or an extracellular fragment thereof. Alternatively, the humanized antibody may be an intact antibody, such as an intact IgG1 antibody.

As an alternative to humanization, human antibodies can be generated. For example, it is possible to produce transgenic animals (e.g., mice) that are capable, upon immunization, of producing a variety of human antibodies in the absence of endogenous immunoglobulin production. See, e.g., Jakobovits et al., Proc. Natl. Acad. Sci. USA, 90:2551 (1993); Jakobovits et al., Nature, 362:255-258 (1993).

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle (See e.g., Johnson, Kevin S. and Chiswell, David J., Current Opinion in Structural Biology 3:564-571 (1993)). Human antibodies may also be generated by in vitro activated B cells (see U.S. Pat. Nos. 5,567,610 and 5,229,275).

Various techniques have been developed for the production of antibody fragments. Traditionally, these fragments were derived via proteolytic digestion of intact antibodies. However, these fragments can also be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries. The antibody fragment may also be a "linear antibody", e.g., as described in U.S. Pat. No. 5,641,870 for example. Such linear antibody fragments may be monospecific or bispecific.

Conjugates of the antibody and a co-stimulatory molecules such as LIGHT may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). An extracellular domain of LIGHT or fragments thereof are conjugated to an antibody or antibody fragments that are specific to a tumor antigen, preferably, a surface tumor antigen.

Alternatively, a fusion protein comprising the anti-tumor antigen antibody and LIGHT may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody-LIGHT complexes disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in U.S. Pat. Nos. 4,485,045 and 4,544,545; and WO97/38731 published Oct. 23, 1997. Liposomes with enhanced circulation time are disclosed in U.S. Pat. No. 5,013,556.

For the prevention or treatment of disease, the dosage and mode of administration will be chosen by the physician according to known criteria. The appropriate dosage of Antibody-LIGHT conjugate or fusion product may depend on the type of cancer to be treated, the severity and course of the disease, the size of the tumor, the extent of metastases, whether the antibody is administered for preventive or therapeutic purposes, previous therapy, the patient's clinical history and response to the antibody, and the discretion of the attending physician. The antibody-LIGHT composition is suitably administered to the patient at one time or over a series of treatments. Preferably, the composition is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen may include administering an initial loading dose of about 5 mg/kg, followed by a weekly maintenance dose of about 2 mg/kg of the anti-TAT antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs, e.g., reduction in tumor size/volume and reduction in metastases. The progress of this therapy can be monitored by conventional methods and assays and based on criteria known to the physician or other persons of skill in the art.

The terms "cancer" and "cancerous" refer to or describe the physiological condition in mammals that is typically characterized by unregulated cell growth. Examples of cancer include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

Suitable surface tumor antigens that can be targeted using a antibody-LIGHT fusion or conjugate includes epidermal growth factor receptor family (EGFR) including HER1, HER2, HER4, and HER8 (Nam, N. H., & Parang, K. (2003), Current targets for anti-cancer drug discovery. Current Drug Targets, 4(2), 159-179), STEAP (six-transmembrane epithelial antigen of the prostate; Hubert et al., STEAP: a prostate-specific cell-surface antigen highly expressed in human prostate tumors, Proc Natl Acad Sci USA. 1999; 96(25): 14523-8.), CD55 (Hsu et al., Generation and characterization of monoclonal antibodies directed against the surface antigens of cervical cancer cells, Hybrid Hybridomics. 2004; 23(2):121-5.). Other suitable antibodies include Rituximab (Rituxan™, a chimeric anti-CD20 antibody), Campath-1H (anti-CD52 antibody), and any cancer specific cell-surface antigens. The following is an exemplary list of approved monoclonal antibody drugs against specific cancer types that are suitable for use with LIGHT protein: Alemtuzumab (Campath™) for chronic lymphocytic leukemia; Bevacizumab (Avastin™) for colon cancer and Lung cancer; Cetuximab (Erbitux™) for colon cancer and head and neck cancer; Gemtuzumab (Mylotarg™) for Acute myelogenous leukemia; Ibritumomab (Zevalin™) for non-Hodgkin's lymphoma; Panitumumab (Vectibix™) for colon cancer; Rituximab (Rituxan™) for Non-Hodgkin's lymphoma; Tositumomab (Bexxar™) for non-Hodgkin's lymphoma; and Trastuzumab (Herceptin™) for breast cancer.

EXAMPLES

The following examples are for illustrative purposes only and are not intended to limit the scope of the disclosure.

Example 1

Coupling or Conjugating LIGHT to a Tumor Targeting Agent

In one aspect of the invention, to enable delivery of a mutant LIGHT delivery system or an equivalent delivery system, mutant LIGHT can be coupled or conjugated to a tumor targeting agent such as a tumor specific antibody. For example, a tumor specific antibody conjugated to LIGHT or mutant LIGHT can be used to selectively deliver the fusion protein to the tumor site. In addition, a tumor specific antibody can be designed to be coupled with a viral delivery system or a liposome vehicle delivery system. The delivery vehicle expressing the mutant LIGHT and harboring the tumor targeting agent will first target the specific tumor cell and then transform the tumor cell to express mutant LIGHT on the surface of the cell. This targeted mutant LIGHT expression on the surface of the tumor cells will induce chemokines on stromal cells surrounding the tumor to attract and initiate priming of T-cells. Such treatments are suitable for all tumors, including solid tumors. 4T1, MC38, B16, and mastocytoma were treated with Ad-LIGHT and showed a reduction of primary and/or secondary tumors. Therefore, antibody-LIGHT can be used to target various tumors, especially metastasis that form as a result of cells of the primary tumor migrating to distant sites. For example, through systemic injection, anti-her2/neu antibody with LIGHT can carry LIGHT to metastatic tumor that expresses her2/neu and then can generate a local immune response to clear tumor. Therefore, the fusion protein can be delivered through any systemic and local route and the fusion protein will be more localized to tumors due to the specificity of antibody or another agent to tumor antigens.

Example 2

Functional Activities of a LIGHT Conjugated Antibody. The ability of antibody-LIGHT to bind to the receptors of LIGHT, LTβR and HVEM, is determined by flow cytometry with LTβR-Ig and HVEM-Ig, respectively. The functional activity of antibody-LIGHT is tested first in vitro for its ability to costimulate T cells in the presence of suboptimal doses of plate-bound anti-CD3. The functionality of antibody-LIGHT seems comparable with that of anti-CD28.

To test whether Antibody-LIGHT fusion protein inhibits tumor growth in vivo, mice are injected s.c. with $5 \times 10^4$ tumor cells for ten days and then treated with 10 µg of the fusion protein. The inhibition of tumor growth is demonstrated by a small dose of fusion protein, i.e. 10 µg. Fusion protein allows strong immunity against tumor.

This example demonstrates the ability of antibody-LIGHT to bind to the receptors of LIGHT, LTβR and HVEM by flow cytometry with LTβR-Ig and HVEM-Ig, respectively and that a tumor specific antibody coupled with LIGHT stimulates immunity to reduce tumor growth.

Example 3

Combination Treatment of Antibody-LIGHT Couple and Local Delivery of Adenovirus Expressing LIGHT An important utility of an antibody-LIGHT fusion protein or conjugate is that such targeting reagents may be very potent to clear small numbers of metastatic tumor cells or residual cancer cells that do not effectively stimulate the immune system. In an aspect of the invention, a combination therapy that includes antibody-LIGHT and adenovirus expressing LIGHT, or Ad-LIGHT, are tested.

Tumor cells are inoculated at two sites, one with $10^6$ and the other side with $1 \times 10^4$. Two weeks later, the larger tumor ($10^6$) is treated with Ad-LIGHT and surgically removed two weeks after treatment. Mice are treated systemically with Antibody-LIGHT at doses described herein. This model determines whether Antibody-LIGHT in combination with local delivery of Ad-LIGHT to primary tumor is a potent reagent for treating distal tumors. 2C T cells, which are readily identified by the clonotypic antibody (1B2), can be adoptively transferred to the tumor bearing mice as a model for tumor antigen-specific $CD8^+$ T cells. The trafficking, proliferation, and activation of adoptively transferred 2C T cells is monitored and compared with different therapeutic strategies.

Two clinically relevant delivery systems, Ad-LIGHT and Antibody-LIGHT are expected to effectively target LIGHT to the tumor tissue and subsequently destroy not only the primary tumors but also distal metastases. The sustained expression of LIGHT long enough to create a LIGHT-mediated lymphoid-like structure induces the desired antitumor $CD8^+$ T cell responses.

Example 4

Anti-Her2/Neu Antibody-LIGHT Therapy for Breast Cancer

One fifth of breast cancer and colon cancer patients express Her2/neu. Generally, antibody to Her2 slows down the growth of these tumors but does not eradicate them. Anti-Her2/neu antibody coupled with LIGHT targets LIGHT to the site of metastatic tumor. The anti-Her2/neu antibody slows down the growth of tumor and induces apoptosis, which allows the coupled LIGHT to induce LIGHT-mediated recruiting and activating of T cells to occur inside tumor. Additionally, LIGHT also recruits FcR+ cells to enhance the therapeutic effect of anti-neu antibody. In an experimental model, doses as low as 10 μg of a tumor antibody linked with LIGHT slowed down the growth of tumor in mice. Other lower or higher doses are contemplated. Anti-Her2/neu antibody-LIGHT is a novel treatment for breast cancer metastases. FIG. 2 that Adv-mmlit inhibits neu+N202 tumor growth.

Example 5

Use of Chemotherapy Drugs in Combination with Antibody-LIGHT Fusion or Conjugates A tumor-specific antibody-LIGHT fusion protein or conjugate is further coupled with an anti-tumor agent such as for example, doxorubicin, paclitaxel, docetaxel, cisplatin, methotrexate, cyclophosphamide, 5-fluoro uridine, Leucovorin, Irinotecan (CAMPTOSAR.TM or CPT-11 or Camptothecin-11 or Campto), Carboplatin, fluorouracil carboplatin, edatrexate, gemcitabine, or vinorelbine or a combination thereof. These drugs can either be administered separately or co-administered by conjugation or coupling with the Antibody-LIGHT fusion protein or conjugate.

This combination therapy may also be co-administered with gene therapy whereby a nucleic acid capable of expressing a protease resistant LIGHT is delivered inside a tumor. Adeno-viral vectors harboring LIGHT nucleic acid sequences, or Ad-LIGHT, are suitable.

Example 6

Synergistic Suppression of Tumors by Anti-Her2 Antibody and Ad-LIGHT Treatment

Figure 4:
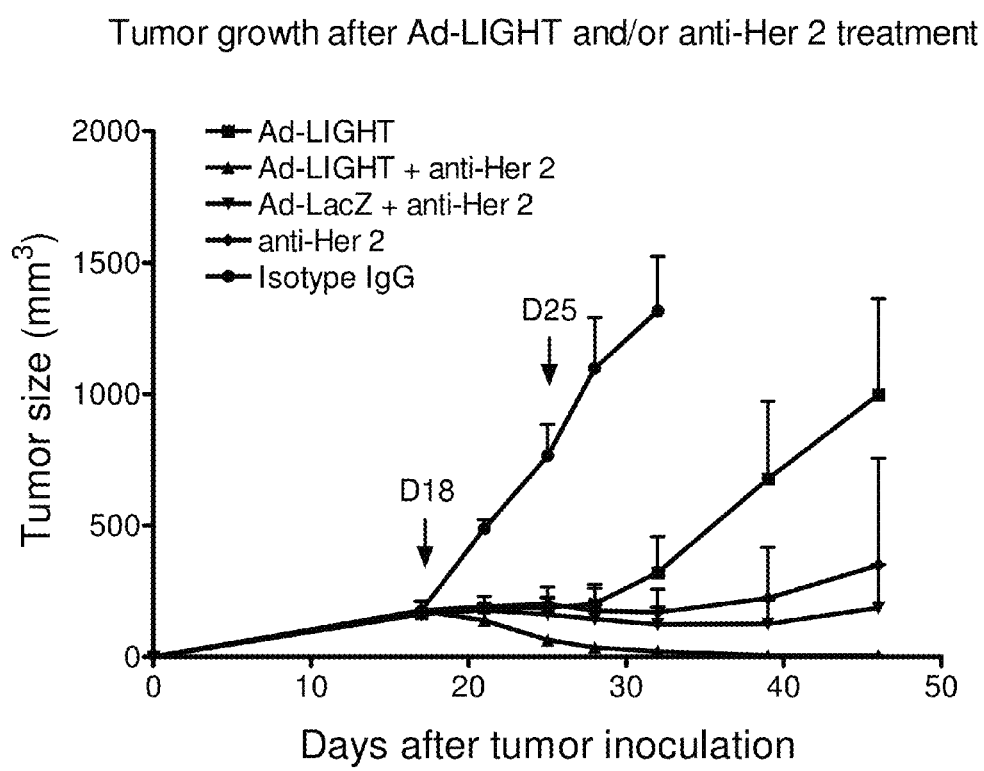
FIG. 4 shows suppression of tumor growth after anti-Her2 and Ad-LIGHT treatment that $10^6$ Tubo tumor cells were inoculated to BABL/c mice s.c. $10^{10}$ VP of Ad-LIGHT or Ad-LacZ was injected intratumor at Day 18 after tumor inoculation. 50 μg anti-Her 2 antibody or isotype IgG was injected i.p. at Day 18 and 25 after tumor inoculation. Tumor growth was monitored at indicated time points. All of the treated groups have significant difference compared with isotype IgG group after Day 21. Ad-LIGHT and anti-Her2 combination treatment group has significant synergistic difference compared with either Ad-LIGHT alone or anti-Her2 alone group after Day 25. Statistic analysis was performed with two-tail student's t test. Data shown were means+SEM. $p<0.05$ was regarded as significant difference.
Figure 5:
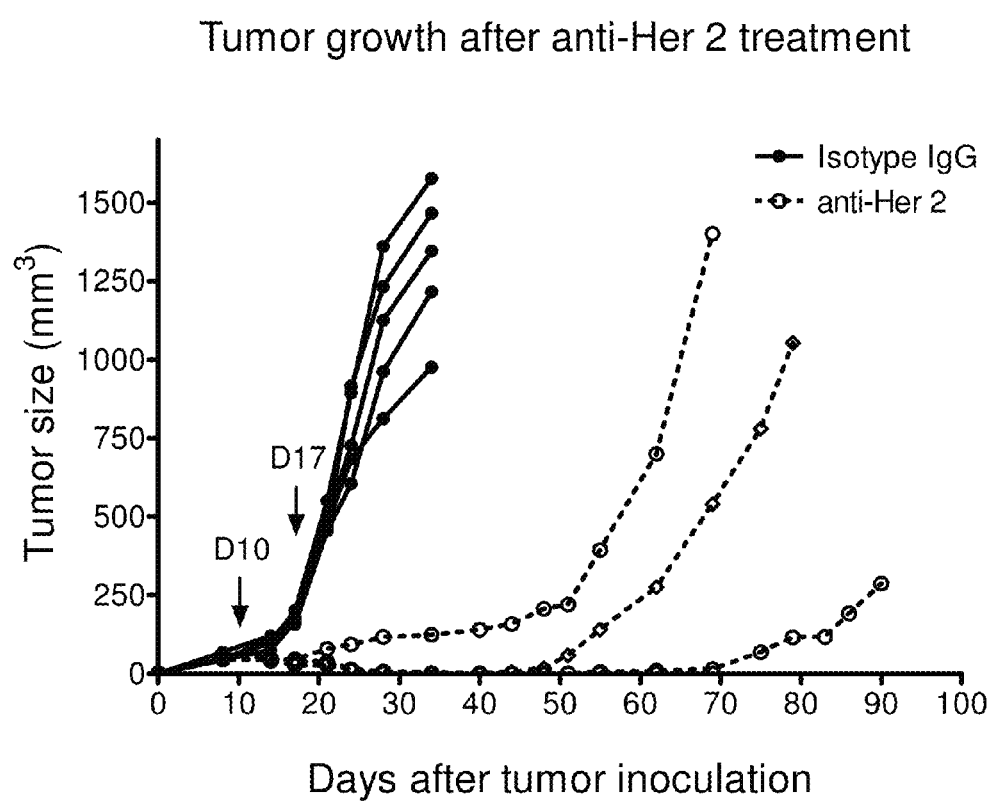
FIG. 5 shows suppression of tumor growth after anti-Her2 treatment. $10^6$ Tubo tumor cells were inoculated to BABL/c mice s.c. 100 μg anti-Her 2 antibody or isotype IgG was injected i.p. at Day 10 and 17 after tumor inoculation. Tumor growth was monitored at indicated time points. Tumor regrew in three out of five mice treated with anti-Her 2.

The synergy of anti-neu antibody with LIGHT. Tubo is the tumor line derived from Balb/c Tg mice overexpressing mutant neu gene. This tumor line is sensitive to antibody treatment in vivo and in vitro. However, when a tumor is well established, the effect of either antibody or LIGHT alone is diminished. After anti-neu antibody is discontinued, tubo regrows in 3-4 weeks. To determine whether there is a synergy between the two, tubo cells were established for 18 days and then treated with both ad-LIGHT and anti-neu antibody once a week for three weeks. Impressively, no tumor can be detected in this combination while tumor grows progressively with single treatment of either (FIGS. 4-5). All five mice in each group have tumors except combinational treatment.

Thus combining LIGHT-mediated therapy, e.g., by Ad-LIGHT expressing vector or by another stable LIGHT presentation to tumor cells with any other anticancer therapy provides a synergistic tumor suppression therapeutics.

Example 7

Generation of Antibody-LIGHT Fusion Proteins

Figure 6:
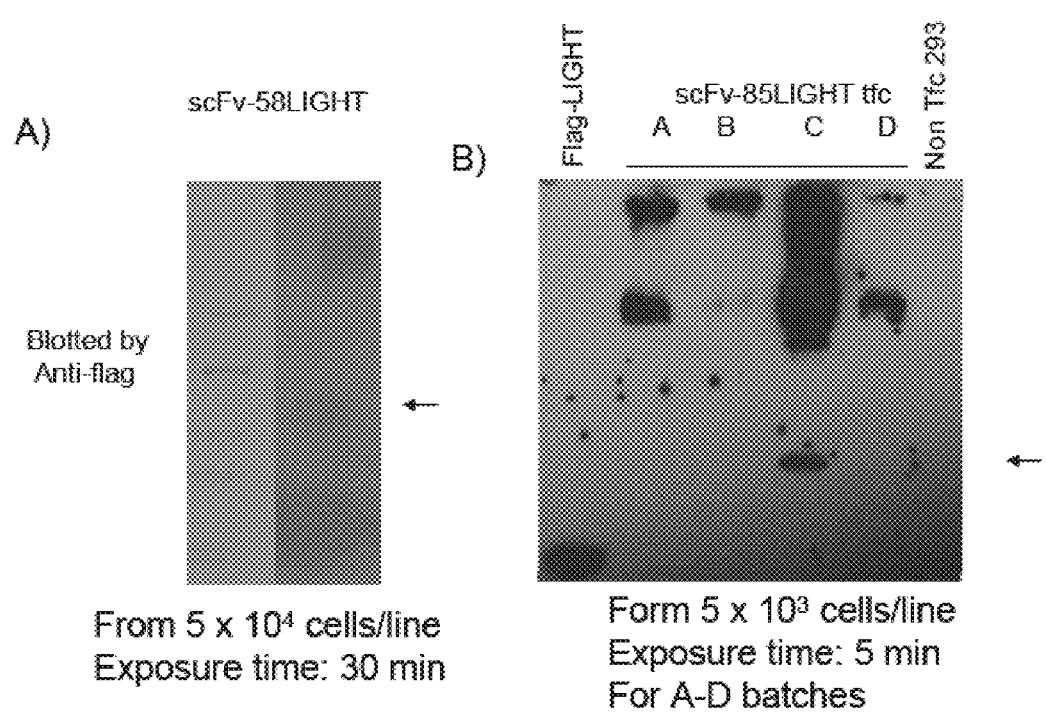
FIG. 6 shows production of antibody-LIGHT fusions. scFV-58LIGHT (LIGHT containing amino acid positions 58-240) and scFV-85LIGHT (LIGHT containing amino acid positions 85-240). The arrow points to the fusion proteins with proper size.

To express sc-Fv-LIGHT, scFV-58LIGHT (LIGHT fragment with amino acid positions 58-240) and scFV-85LIGHT (LIGHT fragment with amino acid positions 85-240, bypassing protease site of 81-84) were constructed. Flag tap was attached to the LIGHT fragment following western blotting since anti-flag antibody is very specific and sensitive. Such plasmids were transfected into a 293 cell line. The cells were harvested one week later and lysates were prepared and blotted with anti-flag antibody. The arrow points to the fusion protein with proper size (FIG. 6). The expression of scFv-85LIGHT expression is higher than scFv-58LIGHT.

This demonstrates that the antibody-LIGHT fusion construct generates fusion proteins and that resulting fusion proteins can be isolated, purified and used to demonstrate that antibody-LIGHT fusion proteins specifically targets tumor cells and stimulates production of T-cells against the tumor cells. Similar fusion proteins of LIGHT can be made with any other antibody that is directed against a tumor cell surface antigen and preferably that targets a tumor-specific cell surface antigen.

Materials and Methods

The Generation of Fusion Protein of Antibody-LIGHT.

A recombinant antibody construct designated heteromini-body was developed that allows for the specific targeting of LIGHT to an antibody that binds to a tumor antigen or tumor cells with high affinity using standard protocol.

Mice, Cell Lines, and Reagents.

Female C3HXC57BL/6 F1 (C3B6F1) mice, 4-8 weeks old were purchased from the National Cancer Institute, Frederick Cancer Research Facility, (Frederick, Md.). C57BL/6-RAG-1-deficient (RAG-1$^{-/-}$) mice were purchased from the Jackson Laboratory (Bar Harbor, Me.). H-Y TCR transgenic mice (H-Y mice) on the RAG-2-deficient/B6 background were purchased from Taconic Farms (Germantown, N.Y.). 2C TCR transgenic mice on RAG-1-deficient background bred into B6 for 10 generations (2C mice) were provided by J. Chen (Massachusetts Institute of Technology, Boston, Mass.). OT-1 TCR transgenic mice (OT-1 mice) were provided by A. Ma (The University of Chicago). RAG-1$^{-/-}$, H-Y, 2C, OT-1 mice were bred and maintained in the specific pathogen-free facility at the University of Chicago Animal care and use were in accord with institutional guidelines.

The AG104A expressing murine H-2L$^d$ (AG104-L$^d$), the transfectant of AG104A cells, has been described previously (Wick M, 1997, JEM). These tumor cell lines were maintained in DMEM (Mediatech) supplemented with 10% FCS (Sigma-Aldrich), 100 U/ml penicillin, and 100 µg/ml streptomycin (BioWhittaker). The hybridoma cell lines producing anti-L$^d$ (clone 30-5-7) and anti-2C TCR (1B2) antibodies were obtained from D. Sachs (National Institutes of Health, Bethesda, Md.) and T. Gajweski (The University of Chicago), respectively.

Monoclonal antibodies produced by hybridomas were purified from the culture supernatant with protein G column by procedures known to those of skill in the art. The antecedent 1B2 antibody was conjugated to FITC or biotin by the Monoclonal Antibody Facility of The University of Chicago. PE-coupled anti-CD8 antibody, Cy-chrome (CyC)-coupled streptavidin, CyC-coupled anti-CD44 antibody, PE-coupled anti-CD62L antibody and PE-coupled Th1.2 antibody were purchased from BD Biosciences. FITC-conjugated-goat-anti-mouse IgG was purchased from Caltag. PE-coupled streptavidin was purchased from Immunotech. PE-coupled donkey anti-human IgG was purchased from Jackson Immunological Research Lab (West grove, PA). Biotinylated goat anti-SLC antibody was purchased from R&D systems Inc. (Minneapolis, Minn.). AP conjugated rabbit anti-goat Ig antibody was purchased from Vector Laboratories Inc. (Burlingame, Calif.). Purified goat anti-SLC antibody was purchased from PeproTech (Rock hill, NJ). Collagenase (type 4) was purchased from Sigma-Aldrich. CFSE was purchased from Molecular Probes. HVEM-Ig and LTBR-Ig fusion proteins used in this study have been described previously.

Tumor Growth In Vivo.

Tumor cells were injected subcutaneously into the lower back, that is, 0.5-1 cm above the tail base of the mice. Tumor growth was measured every 3 to 4 days with a caliper. Size in cubic centimeters was calculated by the formula V=πabc/6, where a, b, and c are three orthogonal diameters.

Histology.

Tumor tissues for histology examination were collected at time indicated and fixed in 10% neutral buffered formalin, processed to paraffin embedment, and stained with hematoxylin and eosin. For immunohistochemical staining of SLC, tumor tissues were harvested, embedded in OCT compound (Miles-Yeda, Rehovot, Israel) and frozen at −70° C. Frozen sections (5-10 µm thick) were fixed in cold 2% formalin in PBS and permeablized with 0.1% saponin/PBS. The sections were preblocked with 5% goat serum in 0.1% saponin/PBS for half an hour at room temperature in a humidified chamber. Staining for SLC was done by first incubating with biotinylated goat anti-SLC antibody (R&D systems Inc Minneapolis, Minn.) at a 1/25 dilution in blocking buffer. Alkaline phosphatase conjugated rabbit anti-goat Ig antibody (Vector Laboratories Inc. Burlingame, Calif.) was added 2 h later. For immunofluorescence staining, sections were blocked with 2% normal mouse serum, rabbit serum, and goat serum in PBS for half an hour at room temperature in a humidified chamber. Blocking solution was replaced with 50 µl of primary Abs, PE-conjugated anti-Th1.2 (BD PharMingen), or PE-conjugated anti-CD8 (BD PharMingen), diluted 1/100 in blocking solution, and sections were incubated for 1 h at room temperature in a humid chamber. Specimens were mounted in Mowiol 4-88 (BD Biosciences, La Jolla, Calif.) containing 10% 1,4-diazobicyclo[2.2.2]octane. Samples were analyzed within 48 h using a Zeiss Axioplan microscope (Zeiss, Oberkochen, Germany) and a Photometrics PXL CCD camera (Photometrics, Tucson, Ariz.). No-neighbor deconvolution was performed using Openlab v2.0.6 (Improvision, Lexington, Mass.).

ELISA for CCL21.

Tumor homogenates were prepared and assayed for CCL21. Comparable amount of tumor tissues from tumor-bearing mice were collected and weighed, homogenized in PBS that contained protease inhibitors, and the supernatants were collected by centrifugation. Polystyrene 96-well microtiter plates (Immulon 4, Dynatech Laboratories, Chantilly, Va.) were coated with goat anti-mouse CCL21 at 2µ µg/ml in PBS and were then blocked with 0.1% bovine serum albumin (BSA) in PBS for 30 min at room temperature. After washing, serial dilutions of standards of known concentrations (Recombinant CCL21, 50 ng/ml, R&D) and samples were added and incubated for 2 h at room temperature. After 3 washes, biotinylated rabbit anti-SLC Ab was added to the wells. After 2 h incubation and washing, 50 µl of a 1/1000 diluted alkaline phosphatase-conjugated avidin (Dako) was added for 1 h and then developed. Color development was measured at 405 nm on an automated plate reader (Spectra-Max 340, Molecular Devices, Sunnyvale, Calif.) and The amount of CCL21 was determined by ELISA from the standard curve, and normalized according to tissue weight. Data are mean±s.d.

T-Cell Co-Stimulation Assay.

T cells were purified by a negative selection method in the magnetic field as instructed by the manufacture (Miltenyi Biotec, Auburn, Calif.). The purity of isolated T cells was greater than 95%, as assessed by flow cytometry using monoclonal antibody against CD3. Plates coated with 0.2 g/ml monoclonal antibody against CD3 were further coated at 37° C. for 4 h with Mutant LIGHT-flag. After being washed, purified T cells (1×10$^6$ cells/ml) were cultured in the wells. Monoclonal antibody against CD28 (1 µg/ml) was used in soluble form. In all assays, the proliferation of T cells was assessed by the addition of 1 Ci/well $^3$H-thymidine during the last 15 h of the 3-day culture. $^3$H-thymidine incorporation was measured in a TopCount microplate scintillation counter (Packard instrument, Meriden, Conn.).

Cell Isolation from Tumor Tissue.

The mice were first bled to decrease the blood contamination of tumor tissue. The tumor tissues were collected, washed in the PBS, cut into pieces, and resuspended in DMEM supplemented with 2% FCS and 1.25 mg/ml collagenase D (collagenase D solution) for 40 min in a 37° C. shaking incubator. The single cell suspension was collected after 40 min, and the cell clumps were digested for another 40 min in the collagenase D solution until all tumor tissue had resolved into a single cell suspension.

Pharmaceutical Compositions:

Therapeutic compositions used herein can be formulated into pharmaceutical compositions comprising a carrier suitable for the desired delivery method. Suitable carriers include materials that when combined with the therapeutic composition retain the anti-tumor function of the therapeutic composition. Examples include a number of standard pharmaceutical carriers such as sterile phosphate buffered saline solutions, bacteriostatic water, and the like. Therapeutic formulations can be solubilized and administered via any route suitable to deliver the therapeutic composition to the tumor site. Potentially effective routes of administration include intravenous, parenteral, intraperitoneal, intramuscular, intratumor, intradermal, intraorgan, orthotopic, and the like. A formulation for intravenous injection includes the therapeutic composition in a solution of preserved bacteriostatic water, sterile unpreserved water, and/or diluted in polyvinylchloride or polyethylene bags containing sterile sodium chloride for injection. Therapeutic protein preparations can be lyophilized and stored as sterile powders, preferably under vacuum, and then reconstituted in bacteriostatic water (containing for example, benzyl alcohol preservative) or in sterile water prior to injection. Dosages and administration protocols for the treatment of cancers using the methods disclosed herein may vary with the method and the target cancer, and generally depend on a number of factors appreciated and understood in the art.

Measurement of Cytokines in the Spleen and Tumor.

Tumor and spleen homogenates was prepared as described (Yu et al., 2003). Briefly, comparable amounts of tumor or spleen tissues were collected, weighed and homogenized in PBS containing protease inhibitors, and the supernatants were collected by centrifugation. The amount of cytokines in the supernatants was quantified using the cytometric bead array kit (CBA) (BD Biosciences) on a FACS Caliber cytometer equipped with CellQuestPro and CBA software (Becton Dickinson) according to manufacture's instruction.

Statistical Analysis for Difference in Tumor Growth.

Because the tumor growth was observed repeatedly over time on the same mouse, the random effect models for longitudinal data were used to analyze such data. For each experiment, the tumor growth was assumed to depend on treatment and to follow a linear growth rate over time. The model gave an overall estimate of the intercept and slope of the linear growth for each group. Both the intercept and slope were allowed to vary among individual mouse. The slope, i.e., the growth rate was compared was different among different treatment groups. Because the actual tumor growth may not follow a linear growth trend over the entire follow up period. The increase of tumor growth was slow at the early stage and became rapid at the later stage in some experiments. A quadratic term was added to the follow-up time in the above random effect models.

Wild type human LIGHT DNA sequence (sequence encoding a protease site EQLI (Residues 81-84 OF SEQ ID NO: 1) is shown in bold):

```
                                           (SEQ ID NO: 3)
ATGGAGGAGAGTGTCGTACGGCCCTCAGTGTTTGTGGTGGATGGACAGAC

AGACCGACATCCCATTCACGAGGCTGGGACGAAGCCACCGGAGACAGTCG

TGCAGTGTGGCCCGGGTGGGTCTGGGTCTCTTGCTGTTGCTGATGGGGGC

TGGGCTGGCCGTCCAAGGCTGGTTCCTCCTGCAGCTGCACTGGCGTCTAG

GAGAGATGGTCACCCGCCTGCCTGACGGACCTGCAGGCTCCTGGGAGCAG

CTGATACAAGAGCGAAGGTCTCACGAGGTCAACCCAGCAGCGCATCTCAC

AGGGGCCAACTCCAGCTTGACCGGCAGCGGGGGGCCGCTGTTATGGGAGA

CTCAGCTGGGCCTGGCCTTCCTGAGGGGCCTCAGCTACCACGATGGGGCC

CTTGTGGTCACCAAAGCTGGCTACTACTACATCTACTCCAAGGTGCAGCT

GGGCGGTGTGGGCTGCCCGCTGGGCCTGGCCAGCACCATCACCCACGGCC

TCTACAAGCGCACACCCCGCTACCCCGAGGAGCTGGAGCTGTTGGTCAGC

CAGCAGTCACCCTGCGGACGGGCCACCAGCAGCTCCCGGGTCTGGTGGGA

CAGCAGCTTCCTGGGTGGTGTGGTACACCTGGAGGCTGGGGAGAAGGTGG

TCGTCCGTGTGCTGGATGAACGCCTGGTTCGACTGCGTGATGGTACCCGG

TCTTACTTCGGGGCTTTCATGGTGTGA-3'.
```

Native human LIGHT amino acid sequence (protease digestion site is bold underlined):

```
                                           (SEQ ID NO: 1)
MEESVVRPSVFVVDGQTDIPFTRLGRSHRRQSCSVVARGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEKVVVRVLDERLVRLRDGTRSYFGAFMV
```

One aspect of a mutant human LIGHT amino acid sequence (EQLI (Residues 81-84 OF SEQ ID NO: 1) is absent, indicated by dots):

```
                                           (SEQ ID NO: 4)
MEESVVRPSVFVVDGQTDIPFTRLGRSHRRQSCSVARVGLGLLLLLMGAG

LAVQGWFLLQLHWRLGEMVTRLPDGPAGSW....QERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEKVVVRVLDERLVRLRDGTRSYFGAFMV.
```

Codon optimized nucleotide sequence (SEQ ID NO: 5) for mouse mutant LIGHT, starting ATG is highlighted in bold:

```
     GGGCGAATTGGGTACCGGATCCGCCACCATGGAGAGCGTGGTGCAGCCCAGCGTGTTCGT

1    ---------+---------+---------+---------+---------+---------+

GGTGGACGGCCAGACCGACATCCCCTTCAGGAGGCTGGAGCAGAACCACAGGCGGAGGAG

61   ---------+---------+---------+---------+---------+---------+

ATGTGGCACCGTGCAGGTGTCCCTGGCCCTGGTGCTGCTGCTGGGCGCTGGCCTGGCCAC
```

```
121 ---------+---------+---------+---------+---------+---------+
CCAGGGCTGGTTTCTGCTGAGGCTGCACCAGAGGCTGGGCGACATCGTGGCCCACCTGCC

181 ---------+---------+---------+---------+---------+---------+
CGATGGCGGCAAGGGCAGCTGGCAGGACCAGAGGAGCCACCAGGCCAACCCTGCCGCCCA

241 ---------+---------+---------+---------+---------+---------+
CCTGACAGGCGCCAACGCCAGCCTGATCGGCATCGGCGGACCCCTGCTGTGGGAGACCAG

301 ---------+---------+---------+---------+---------+---------+
GCTGGGCCTGGCTTTCCTGAGGGGCCTGACCTACCACGACGGCGCCCTGGTGACCATGGA

361 ---------+---------+---------+---------+---------+---------+
GCCCGGCTACTACTACGTGTACAGCAAGGTGCAGCTGTCCGGAGTGGGCTGCCCTCAGGG

421 ---------+---------+---------+---------+---------+---------+
CCTGGCCAACGGCCTGCCCATCACCCACGGCCTGTACAAGAGGACCAGCAGATACCCCAA

481 ---------+---------+---------+---------+---------+---------+
GGAGCTGGAGCTGCTGGTCTCCAGGCGGAGCCCCTGTGGCAGGGCCAACAGCAGCCGAGT

541 ---------+---------+---------+---------+---------+---------+
GTGGTGGGACAGCAGCTTCCTGGGCGGCGTGGTGCACCTGGAGGCCGGCGAGGAGGTGGT

601 ---------+---------+---------+---------+---------+---------+
GGTGAGGGTGCCCGGCAACAGGCTGGTGAGGCCCAGGGACGGCACCAGGAGCTACTTCGG

661 ---------+---------+---------+---------+---------+---------+
CGCCTTCATGGTGTGATGAGCGGCCGCGAGCTCCAGCTTTTGTTCCC

721 ---------+---------+---------+---------+-------
GCGGAAGTACCACACTACTCGCCGGCGCTCGAGGTCGAAAACAAGGG
```

Codon optimized nucleotide sequence for human mutant LIGHT (SEQ ID NO: 6), starting ATG is highlighted in bold.

```
GAATTCGAGCTCGGTACCCGACACGGTACCGGATCCGCCACCATGGAGGA
GAGCGTTGTGAGGCCCAGCGTGTTCGTGGTGGACGGCCAGACCGACATCC
CCTTCACCCGGCTGGGCCGGAGCCACCGGAGGCAGAGCTGCTCCGTGGCC
AGAGTGGGGCTGGGCCTGCTGCTCCTGCTGATGGGAGCCGGCCTGGCCGT
GCAGGGCTGGTTCCTGCTGCAGCTGCACTGGCGGCTGGGCGAGATGGTGA
CCCGGCTGCCCGATGGCCCTGCCGGCAGCTGGCAGGAGCGGCGGAGCCAC
GAGGTGAACCCTGCCGCCCACCTGACCGGCGCCAACAGCAGCCTGACCGG
CAGCGGCGGACCCCTGCTGTGGGAGACCCAGCTGGGCCTGGCCTTCCTGA
GGGGCCTGAGCTACCACGACGCGCCCTGGTGGTGACCAAGGCCGGCTAC
TACTACATCTACAGCAAGGTGCAGCTGGGCGGAGTGGGCTGCCCTCTGGG
GCTGGCCAGCACCATCACCCACGGCCTGTACAAGCGGACCCCCAGATACC
CCGAGGAGCTGGAGCTGCTGGTGTCCCAGCAGAGCCCCTGTGGCAGGGCC
ACCTCCAGCAGCCGGGTGTGGTGGGACAGCAGCTTCCTGGGCGGCGTGGT
GCACCTGGAGGCCGGCGAGAAAGTGGTTGTGAGGGTGCTGGACGAGCGGC
```
-continued
```
TTGTGAGGCTGAGGGACGGCACCCGGAGCTACTTCGGCGCCTTCATGGTG
TGATGAGCGGCCGCGAGCTCGTCTCGGGGATCCTCTAGAGTCGACCTGCA
GGCATGCAAGCTTG
```

Generation of mutant LIGHT Expression Vectors and Clones pcDNA3.1-LIGHT was used as template to generate two dsDNA fragments A and B by PCR. For generation of fragment A (~500 b.p.), sense primer 5'-CATGGATC-CAAGACCATGGAGAGTGTGGTACA-3' (SEQ ID NO: 7) (the bold text indicated BamHI site) and antisense primer 5'-AGATCGTTGATCTTGCCAGGAGCCTTTGCC-3' (SEQ ID NO: 8) were used. To generate fragment B (~200 b.p.), sense primer 5'-GGCAAAGGCTCCTGGCAAGAT-CAACGATCT-3' (SEQ ID NO: 9) and antisense primer 5'-ACCTCTAGATCAGACCATGAAAGCTCCGA-3' (SEQ ID NO: 10) (the underlined text indicated XbaI site) were used. The antisense primer for fragment A is complimentary with sense primer for fragment B, which covers sequences for amino acid (a.a.) 73-87 among which a.a. 79-82 were deleted. Fragments A and B were mixed, denatured at 94° C. and cooled down to room temperature to anneal the two DNA fragments. The annealed DNA product was used as template for a PCR reaction and the product was cloned into pcDNA3.1 using BamHI and XbaI. The deletion of a.a. 79-82 was verified by sequencing. To generate pMFG-mutant LIGHT, pcDNA3.1-mutant LIGHT was digested with NcoI and BamHI and ligated to a NcoI and BamHI-digested the pMFG-S-TPA plasmid (Mulligan R C, Massachusetts Institute of Technology, Boston, Mass.).

The invention claimed is:

1. A method of reducing the growth of a primary tumor or cancer metastasis in a subject in need thereof, the method comprising:
   (a) administering to the subject a composition comprising a tumor specific antibody linked to a fragment of a human LIGHT protein to the subject, wherein the LIGHT fragment is resistant to protease digestion and is sufficient to stimulate tumor specific cytotoxic T lymphocytes against the tumor cells;
   (b) delivering a nucleic acid molecule encoding LIGHT or a fragment thereof to the primary tumor; and
   (c) stimulating the tumor-specific cytotoxic T-lymphocytes against the tumor or its metastases to reduce to the growth of the primary tumor or cancer metastasis.

2. The method of claim 1, wherein the nucleic acid molecule is delivered to a pre-existing tumor site or to a site distal to a pre-existing tumor site.

3. A method of reducing the growth of a primary tumor or cancer metastasis in a subject in need thereof, the method comprising:
   (a) administering to the subject a pharmaceutical composition comprising a tumor-specific antibody;
   (b) delivering a nucleic acid molecule encoding a LIGHT protein or a fragment thereof to the tumor, wherein the LIGHT is protease resistant;
   (c) expressing the LIGHT protein or a fragment thereof stably on the surface of the tumor; and
   (d) stimulating activation of tumor-specific cytotoxic T-lymphocytes against the tumor to reduce the growth of the tumor or cancer metastasis.

4. A method of reducing the growth of a primary tumor or cancer metastasis in a subject in need thereof, the method comprising:
   (a) administering to the subject a pharmaceutical composition comprising a tumor-specific antibody;
   (b) delivering a nucleic acid molecule encoding a protease resistant LIGHT or a fragment thereof to the primary tumor; and
   (c) stimulating activation of tumor-specific cytotoxic T-lymphocytes against the tumor to reduce the growth of the tumor and cancer metastasis.

5. The method of claim 4, wherein the nucleic acid is delivered to a pre-existing tumor site or at a site distal to the pre-existing tumor site.

6. The method of claim 3, wherein the nucleic acid is delivered to a pre-existing tumor site or at a site distal to the pre-existing tumor site.

7. A method of reducing the growth of a primary tumor or cancer metastasis in a subject in need thereof, the method comprising:
   (a) administering to the subject a composition comprising a tumor specific antibody linked to a fragment of a human LIGHT protein, wherein the LIGHT fragment is resistant to protease digestion and is sufficient to stimulate cytotoxic T lymphocytes against the tumor;
   (b) delivering a nucleic acid molecule encoding a LIGHT protein or a fragment thereof to the tumor, wherein the LIGHT is protease resistant;
   (c) expressing the LIGHT protein or a fragment thereof stably on the surface of the tumor; and
   (d) stimulating activation of tumor-specific cytotoxic T-lymphocytes against the tumor or metastatic cells to reduce the growth of the tumor or cancer metastasis.

8. The method of claim 7, wherein the nucleic acid is delivered to a pre-existing tumor site or to a site distal to the pre-existing tumor site.

* * * * *

UNITED STATES PATENT AND TRADEMARK OFFICE
CERTIFICATE OF CORRECTION

PATENT NO. : 9,623,116 B2
APPLICATION NO. : 14/717808
DATED : April 18, 2017
INVENTOR(S) : Yang-Xin Fu It is certified that error appears in the above-identified patent and that said Letters Patent is hereby corrected as shown below:

In the Specification

In Column 1, Line 15, please insert the following government funding statement:
-- This invention was made with government support under AI057153, and CA097296 awarded by the National Institutes of Health. The government has certain rights in the invention --

Signed and Sealed this
Sixteenth Day of April, 2024

Katherine Kelly Vidal
*Director of the United States Patent and Trademark Office*

SEQUENCE LISTING

<160> NUMBER OF SEQ ID NOS: 12

<210> SEQ ID NO 1
<211> LENGTH: 240
<212> TYPE: PRT
<213> ORGANISM: Homo sapiens

<400> SEQUENCE: 1

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 2
<211> LENGTH: 181
<212> TYPE: PRT
<213> ORGANISM: Homo sapiens

<400> SEQUENCE: 2

Gln Leu His Trp Arg Leu Gly Glu Met Val Thr Arg Leu Pro Asp Gly
1               5                   10                  15

Pro Ala Gly Ser Trp Glu Gln Leu Ile Gln Glu Arg Arg Ser His Glu
            20                  25                  30

Val Asn Pro Ala Ala His Leu Thr Gly Ala Asn Ser Ser Leu Thr Gly
        35                  40                  45

Ser Gly Gly Pro Leu Leu Trp Glu Thr Gln Leu Gly Leu Ala Phe Leu
    50                  55                  60

Arg Gly Leu Ser Tyr His Asp Gly Ala Leu Val Val Thr Lys Ala Gly
65                  70                  75                  80

Tyr Tyr Tyr Ile Tyr Ser Lys Val Gln Leu Gly Gly Val Gly Cys Pro

```
                    85                  90                  95

Leu Gly Leu Ala Ser Thr Ile Thr His Gly Leu Tyr Lys Arg Thr Pro
            100                 105                 110

Arg Tyr Pro Glu Glu Leu Glu Leu Leu Val Ser Gln Gln Ser Pro Cys
        115                 120                 125

Gly Arg Ala Thr Ser Ser Ser Arg Val Trp Trp Asp Ser Ser Phe Leu
    130                 135                 140

Gly Gly Val Val His Leu Glu Ala Gly Glu Lys Val Val Val Arg Val
145                 150                 155                 160

Leu Asp Glu Arg Leu Val Arg Leu Arg Asp Gly Thr Arg Ser Tyr Phe
                165                 170                 175

Gly Ala Phe Met Val
            180

<210> SEQ ID NO 3
<211> LENGTH: 723
<212> TYPE: DNA
<213> ORGANISM: Homo sapiens

<400> SEQUENCE: 3
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggctggg ctggccgtcc aaggctggtt cctcctgcag     180
ctgcactggc gtctaggaga gatggtcacc cgcctgcctg acggacctgc aggctcctgg     240
gagcagctga tacaagagcg aaggtctcac gaggtcaacc cagcagcgca tctcacaggg     300
gccaactcca gcttgaccgg cagcgggggg ccgctgttat gggagactca gctgggcctg     360
gccttcctga ggggcctcag ctaccacgat gggcccttg tggtcaccaa agctggctac     420
tactacatct actccaaggt gcagctgggc ggtgtgggct gcccgctggg cctggccagc     480
accatcaccc cacggcctcta caagcgcaca ccccgctacc ccgaggagct ggagctgttg     540
gtcagccagc agtcaccctg cggacgggcc accagcagct cccgggtctg gtgggacagc     600
agcttcctgg gtggtgtggt acacctggag gctggggaga aggtggtcgt ccgtgtgctg     660
gatgaacgcc tggttcgact gcgtgatggt acccggtctt acttcggggc tttcatggtg     720
tga                                                                    723

<210> SEQ ID NO 4
<211> LENGTH: 236
<212> TYPE: PRT
<213> ORGANISM: Homo sapiens

<400> SEQUENCE: 4

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Gln Glu Arg Arg Ser His Glu Val Asn Pro Ala Ala His Leu Thr Gly
                85                  90                  95
```

Ala Asn Ser Ser Leu Thr Gly Ser Gly Gly Pro Leu Leu Trp Glu Thr
            100                 105                 110

Gln Leu Gly Leu Ala Phe Leu Arg Gly Leu Ser Tyr His Asp Gly Ala
            115                 120                 125

Leu Val Val Thr Lys Ala Gly Tyr Tyr Ile Tyr Ser Lys Val Gln
145         130                 135                 140

Leu Gly Gly Val Gly Cys Pro Leu Gly Leu Ala Ser Thr Ile Thr His
145                 150                 155                 160

Gly Leu Tyr Lys Arg Thr Pro Arg Tyr Pro Glu Glu Leu Glu Leu Leu
            165                 170                 175

Val Ser Gln Gln Ser Pro Cys Gly Arg Ala Thr Ser Ser Ser Arg Val
            180                 185                 190

Trp Trp Asp Ser Ser Phe Leu Gly Gly Val Val His Leu Glu Ala Gly
            195                 200                 205

Glu Lys Val Val Val Arg Val Leu Asp Glu Arg Leu Val Arg Leu Arg
            210                 215                 220

Asp Gly Thr Arg Ser Tyr Phe Gly Ala Phe Met Val
225                 230                 235

<210> SEQ ID NO 5
<211> LENGTH: 814
<212> TYPE: DNA
<213> ORGANISM: Mus sp.

<400> SEQUENCE: 5
gggcgaattg ggtaccggat ccgccaccat ggagagcgtg gtgcagccca gcgtgttcgt      60
ggtggacggc cagaccgaca tccccttcag gaggctggag cagaaccaca ggcggaggag     120
atgtggcacc gtgcaggtgt ccctggccct ggtgctgctg ctgggcgctg gcctggccac     180
ccagggctgg tttctgctga ggctgcacca gaggctgggc gacatcgtgg cccacctgcc     240
cgatggcgga aagggcagct ggcaggacca gaggagccac caggccaacc ctgccgccca     300
cctgacaggc gccaacgcca gcctgatcgg catcggcgga ccctgctgt gggagaccag     360 gctgggcctg gctttcctga ggggcctgac ctaccacgac ggcgccctgg tgaccatgga     420
gcccggctac tactacgtgt acagcaaggt gcagctgtcc ggagtgggct gccctcaggg     480
cctggccaac ggcctgccca tcacccacgg cctgtacaag aggaccagca gatacccaa     540 ggagctggag ctgctggtct ccaggcggag ccctgtggc agggccaaca gcagccgagt     600
gtggtgggac agcagcttcc tgggcggcgt ggtgcacctg gaggcggcg aggaggtggt     660 ggtgagggtg cccggcaaca ggctggtgag gcccagggac ggcaccagga gctacttcgg     720
cgccttcatg gtgtgatgag cggccgcgag ctccagcttt tgttcccgcg aagtaccac     780 actactcgcc ggcgctcgag gtcgaaaaca aggg                                 814

<210> SEQ ID NO 6
<211> LENGTH: 814
<212> TYPE: DNA
<213> ORGANISM: Homo sapiens

<400> SEQUENCE: 6
gaattcgagc tcggtacccg acacggtacc ggatccgcca ccatggagga gagcgttgtg      60
aggcccagcg tgttcgtggt ggacggccag accgacatcc ccttcacccg gctgggccgg     120
agccaccgga ggcagagctg ctccgtggcc agagtgggc tgggcctgct gctcctgctg     180
atgggagccg gcctggccgt gcagggctgg ttcctgctgc agctgcactg gcggctgggc     240

```
gagatggtga cccggctgcc cgatggccct gccggcagct ggcaggagcg gcggagccac      300
gaggtgaacc ctgccgccca cctgaccggc gccaacagca gcctgaccgg cagcggcgga      360
cccctgctgt gggagaccca gctgggcctg gccttcctga ggggcctgag ctaccacgac      420
ggcgccctgg tggtgaccaa ggccggctac tactacatct acagcaaggt gcagctgggc      480
ggagtgggct gccctctggg gctggccagc accatcaccc acggcctgta caagcggacc      540
cccagatacc ccgaggagct ggagctgctg gtgtcccagc agagccctg tggcagggcc       600 acctccagca gccgggtgtg gtgggacagc agcttcctgg cggcgtggt gcacctggag       660 gccggcgaga aagtggttgt gagggtgctg gacgagcggc ttgtgaggct gagggacggc      720
acccggagct acttcggcgc cttcatggtg tgatgagcgg ccgcgagctc gtctcgggga     780
tcctctagag tcgacctgca ggcatgcaag cttg                                  814
```

```
<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggatcca agaccatgga gagtgtggta ca                                    32

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agatcgttga tcttgccagg agcctttgcc                                       30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcaaaggct cctggcaaga tcaacgatct                                       30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acctctagat cagaccatga aagctccga                                        29

<210> SEQ ID NO 11
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 11

Arg Thr Val Ala Ala
 1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser Gly Gly Gly Gly Ser
 1               5                  10                  15
```